United States Patent
Saji et al.

(10) Patent No.: US 10,794,920 B2
(45) Date of Patent: *Oct. 6, 2020

(54) PREGNANCY TEST DEVICE AND METHOD

(71) Applicant: SPD Swiss Precision Diagnostics GMBH, Geneva (CH)

(72) Inventors: Eapen Saji, Cambridgeshire (GB); David McCarthy, Bedford (GB)

(73) Assignee: SPD Swiss Precision Diagnostics GmbH, Geneva (CH)

( * ) Notice: Subject to any disclaimer, the term of this patent is extended or adjusted under 35 U.S.C. 154(b) by 196 days.

This patent is subject to a terminal disclaimer.

(21) Appl. No.: 15/563,784

(22) PCT Filed: Apr. 4, 2016

(86) PCT No.: PCT/IB2016/000500
§ 371 (c)(1),
(2) Date: Oct. 2, 2017

(87) PCT Pub. No.: WO2016/156981
PCT Pub. Date: Oct. 6, 2016

(65) Prior Publication Data
US 2018/0088136 A1 Mar. 29, 2018

Related U.S. Application Data

(60) Provisional application No. 62/142,297, filed on Apr. 2, 2015.

(51) Int. Cl.
*G01N 33/76* (2006.01)
*G01N 33/558* (2006.01)
(Continued)

(52) U.S. Cl.
CPC .......... *G01N 33/76* (2013.01); *G01N 33/558* (2013.01); *G01N 33/689* (2013.01); *G01N 33/743* (2013.01); *G01N 2333/59* (2013.01)

(58) Field of Classification Search
CPC .... G01N 33/76; G01N 33/558; G01N 33/689; G01N 33/743; G01N 2333/59
See application file for complete search history.

(56) References Cited

U.S. PATENT DOCUMENTS 5,786,220 A 7/1998 Pronovost et al.
7,090,802 B1 * 8/2006 Wang .................... B01L 3/5023
422/417

(Continued)

FOREIGN PATENT DOCUMENTS

CN 108459167 A 8/2018
EP 0075193 A1 3/1983
(Continued)

OTHER PUBLICATIONS

Fang et al. Comparison of Gestational Period Reproductive Hormone Levels between Women in Groups of Normal Pregnancy, Spontaneous Abortion and Early Fetal Loss. Reproduction and Contraception 25 (3): 1-4 (Jan. 2005).*

(Continued)

*Primary Examiner* — Gailene Gabel
(74) *Attorney, Agent, or Firm* — Erik Huestis; Foley Hoag LLP

(57) ABSTRACT

Disclosed is a test device to detect pregnancy In a human female subject, the test device comprising: an assay means to measure the absolute or relative amount of hCG m a sample from the subject; an assay means to measure the absolute or relative amount of FSH in a sample from the subject; and m assay means to measure the absolute or relative amount of one or mere progesterone metabolites I>> a sample from the subject.

10 Claims, 6 Drawing Sheets

(51) Int. Cl.
*G01N 33/74* (2006.01)
*G01N 33/68* (2006.01)

(56) References Cited

U.S. PATENT DOCUMENTS

| | | | |
|---|---|---|---|
| 7,572,639 | B2 | 8/2009 | Cole et al. |
| 7,700,372 | B2 | 4/2010 | Nylese |
| 8,721,990 | B2 * | 5/2014 | Raj ..................... G01N 33/558 422/400 |
| 10,228,377 | B2 * | 3/2019 | McCarthy ............ G01N 33/689 |
| 2006/0019404 | A1 | 1/2006 | Blatt et al. |
| 2009/0061534 | A1 | 3/2009 | Sharrock |
| 2010/0129935 | A1 | 5/2010 | Maddison |
| 2012/0021531 | A1 | 1/2012 | Ellis et al. |
| 2013/0065321 | A1 | 3/2013 | Nazareth et al. |
| 2013/0217136 | A1 | 8/2013 | Nazareth et al. |

FOREIGN PATENT DOCUMENTS

| | | |
|---|---|---|
| EP | 1484601 A2 | 12/2004 |
| EP | 1920250 A1 | 5/2008 |
| EP | 2031376 A2 | 3/2009 |
| GB | 2335983 A | 10/1999 |
| RU | 2398235 C2 | 8/2010 |
| WO | WO-1996/27800 A1 | 9/1996 |
| WO | WO-1996/34287 A1 | 10/1996 |
| WO | WO-1999/51989 A1 | 10/1999 |
| WO | WO-03/025582 A1 | 3/2003 |
| WO | WO-03/079011 A2 | 9/2003 |
| WO | WO-2007/025558 A1 | 3/2007 |
| WO | WO-2008/122796 A1 | 10/2008 |
| WO | WO-2010/055355 A1 | 5/2010 |
| WO | WO-2013/178739 A1 | 12/2013 |
| WO | WO-2014/047692 A1 | 4/2014 |
| WO | WO-2015/049508 A1 | 4/2015 |

OTHER PUBLICATIONS

Notice of Allowance for U.S. Appl. No. 14/505,083 dated Oct. 18, 2018.
Fang et al., "Comparison of Gestational Period Reproductive Hormone Levels between Women in Groups of Normal Pregnancy, Spontateous Abortion and Early Fetal Loss," Shengzhi Yu Biyun—Reproduction and Contraception, Shanghai Jihua Shengyu Kexue Yanjiusuo, Shanghai, CN; 25(3): 155-158 (Jan. 1, 2005).
Gronowski et al., "Use of serum FSH to identify perimenopausal women with pituitary hCG," Clin Chem, 54(4):652-656 (2008).
International Search Report and Written Opinion for International Application No. PCT/IB2016/000500 dated Jul. 5, 2016.
International Search Report for PCT/GB2014/052960 dated Jan. 26, 2015.
Jeppsson et al., "Pituitary gonadotrophin secretion during the first weeks of pregnancy," Acta Endocrinol, 85: 177-188 (1977).
McCudden et al., "Persistent low concentration of human chorionic gonadotropin in a nonpregnant woman," Clin Chem, 54(1): 209-214 (2008).
Phipps et al., "Progesterone, inhibin, and hCG multiple marker strategy to differentiate viable from nonviable pregnancies," Obstet Gynecol, 95(2):227-231 (2000).
Qiu et al., "Total urinary follicle stimulating hormone as a biomarker for detection of early pregnancy and periimplantation spontaneous abortion," Environmental Health Perspectives, 105(8): 862-866 (1997).
Shimizu, "Studies on Reproductive Endocrinology in Non-human Primates: Application of Non-invasive Methods," J Reprod Develop, 51(1):1-13 (2005).
Synder et al., "Diagnostic Considerations in the Measurement of Human Chorionic Gonadotropin in Aging Women," Clin Chem, 51(10): 1830-1835 (2005).
UK Search Report for GB1317458.6 dated Apr. 8, 2014.

* cited by examiner

PREGNANCY TEST DEVICE AND METHOD

FIELD OF THE INVENTION

The present invention relates to a pregnancy test device, and to a method of performing a pregnancy test, and to a method of making the device.

BACKGROUND OF THE INVENTION

Simple lateral flow immunoassay devices have been developed and commercialised for detection of analytes in fluid samples, see for example EP291194. Such devices typically comprise a porous carrier comprising a dried, mobilisable labelled binding reagent capable of binding to the analyte in question, and an immobilised binding reagent also capable of binding to the analyte provided at a detection zone downstream from the labelled binding reagent. Detection of the immobilised labelled binding reagent at the detection zone provides an indication of the presence of analyte in the sample.

Alternatively, when the analyte of interest is a hapten, the immunoassay device may employ a competition reaction wherein a labelled analyte or analyte analogue competes with analyte present in the sample for binding to an immobilised binding reagent at a detection zone. Alternatively the assay device may employ an inhibition reaction whereby an immobilised analyte or analyte analogue is provided at a detection zone, the assay device comprising a mobilisable labelled binding reagent for the analyte.

An assay device may be able to detect the presence and/or amount of more than one analyte. For example, in the case of assays detecting the presence of drugs of abuse, the device may be capable of determining a whole panel of drugs. Such lateral flow immunoassay devices are generally provided with multiple detection zones, such zones being provided on a single or multiple lateral flow carriers, within the assay device.

Determination of the result of the assay has been traditionally carried out by eye. However such devices require the result to be interpreted by the user which introduces an undesirable degree of subjectivity, particularly at low analyte levels when the intensity of the detection zone is faint.

As such, digital devices have been developed comprising an optical detection means arranged to determine the result of the assay as well as a display means to display the result of the assay. Digital assay readers for use in combination with assay test-strips for determining the concentration and/or amount of analyte in a fluid sample are known as are assay devices comprising an integral digital assay reader. An example of such a device is disclosed in EP 1484601.

Light from a light source, such as a light emitting diode (LED), is shone onto a portion of the porous carrier and either reflected or transmitted light is detected by a photodetector. Typically, the reader will have more than one LED to illuminate various zones of the carrier, and a corresponding photodetector is provided for each of the plurality of LEDs. EP1484601 discloses an optical arrangement for a lateral flow test strip digital reading device comprising a baffle arrangement allowing for the possibility of reducing the number of photodetectors in the device.

Assay technology of the foregoing type has been implemented into "self-test" pregnancy testing devices. These are, typically, devices which are used by women who suspect they may be pregnant. As such, they must be designed in such a way that they are easy to use (not requiring any medical or technical training), and are typically disposable after a single use. The device is usually a lateral flow immunoassay device, and normally the test is initiated by contacting a sampling portion of a lateral flow assay stick with a urine sample. The sampling portion of the assay stick may be immersed into a sample of urine in a container or, more typically, the user may urinate directly onto the sampling portion. The assay then runs without the woman needing to perform any further steps, and the result is indicated and read by eye or, in a digital device, is determined by an assay result reading means and displayed to the user, by means of a display such as, for example, a liquid crystal display (LCD).

Conventional pregnancy tests of this sort work by measuring human chorionic gonadotrophin (hCG) in the sample. The hCG is produced by the developing embryo and a concentration of hCG in fee sample above a certain threshold will trigger a positive (i.e. "pregnant") result.

There is a need for an improved pregnancy test, especially an improved self-test pregnancy test: many women wish to know, as son as possible, if they are pregnant, and there is a need therefore for a very sensitive test, which can detect hCG in samples, such as urine, at very low concentration. However, this creates a problem because hCG can sometimes be present in urine, at relatively low concentration, for reasons other than pregnancy, such that a very sensitive pregnancy test may give a false positive result (i.e. the specificity of the assay is diminished).

As an illustration of this, non-pregnancy associated hCG may be present in a urine sample. More especially, hCG may be present in urine from peri-menopausal and post-menopausal women, and derives from the pituitary rather than a developing embryo. The detection of this pituitary gland-derived hCG, or other non-pregnancy associated hCG, in a pregnancy test will give rise to a false positive result for pregnancy. In many countries, women defer stating a family until later in life e.g. due to work or other commitments, and so a small but significant market for 'home' or self-test pregnancy test devices is constituted by older women who may fall into the peri-menopausal or post-menopausal bracket, and are therefore susceptible to false positive results if using a sensitive hCG assay. According to one study, up to 10% of the sales of OTC pregnancy tests have been to women >40 yrs old (Leavitt S A 2004 "A private little revolution: the home pregnancy test in American Culture". Bull, Hist. Med. 2006; 80:317-45).

According to the World Health Organization, the recognized definitions of "menopause" and "perimenopause" are as follows:

Menopause (natural menopause)—is defined as the permanent cessation of menstruation resulting from the loss of ovarian follicular activity. Natural menopause is recognized to have occurred after 12 consecutive months of amenorrhea, for which there is no other obvious pathological or physiological cause. Menopause occurs with the final menstrual period (FMP) which is known with certainty only in retrospect a year or more after the event.

Perimenopause—the term perimenopause includes the period immediately prior to the menopause (when the endocrinological, biological, and clinical features of approaching menopause commence) and the first year after menopause.

Accordingly, for present purposes, peri-menopausal women are defined as being those women also are in peri-menopause according to the WHO definition above and post-menopausal women are defined as those who have undergone menopause according to the WHO definition above.

Self-test or 'home' pregnancy tests need to be reliable to ensure women take appropriate action on receiving their test result. A desirable reliability target is ≥99% accuracy (i.e. a combined false positive and false negative rate of 1% or less). Currently available self-test or home test devices can detect urinary hCG at a concentration of 25 mIU/ml or more with a sensitivity of ≥99%. Such devices can achieve the desired ≥99% accuracy target, but only if used on the day the subject expects her period to start (i.e. expected first day of menstrual bleeding), or later, because from that point nearly all women who are pregnant will have a urinary hCG concentration of 25 mIU/ml or greater, and levels of non-pregnancy associated hCG never normally attain this level. However, it follows that if a woman uses a self-test device before her day of expected period, a false negative result is possible because the urinary hCG concentration has not yet reached a level detectable by the test. Accordingly, currently-available conventional self-test pregnancy test devices are not 99% accurate when used before the day of expected period. In fact the median level of hCG in urine 10 days following ovulation is about 8.4 mIU/ml, and only about 10% of samples from this day would have a hCG concentration >25 mIU/ml. Therefore, a very low pregnancy detection rate would be seen using a conventional self-test device with 25 mIU/ml sensitivity this early in pregnancy. At 11 days following ovulation, median level rises to 19.8 mIU/ml, so at this stage less than 50% of women would be likely to receive a positive result. Detection rates for later testing would be approximately 70% (day 12), 80% (day 13) and nearly 100% (day 14), based on a 25 mIU/ml test sensitivity. Simply using a more sensitive test is not a solution, since this would increase the risk of a false positive result, due to increased likelihood of detecting non-pregnancy associated hCG, so the test would still not be ≥99% accurate.

There exists therefore a need for a pregnancy test device, especially a self-test or home test device, which is able to detect pregnancy with ≥99% accuracy, even when used at a time point earlier in pregnancy than the day of expected period.

In a different context, in many countries, tests for serum hCG are routinely performed on nearly all women patients of child-bearing age before conducting any medical intervention which might harm a developing foetus. The problem of elevated serum hCG levels, "pituitary" hCG, in peri- and post-menopausal women is recognised. Snyder et al., (Clinical Chemistry 2005 51, 1830-1835) examined changes with age in serum hCG concentrations of non-pregnant women and investigated the use of serum follicle-stimulating hormone (FSH) measurements as an aid to interpreting higher than expected hCG results. They suggested, that a combination of serum hCG measurement, knowledge of the age of the subject, and serum FSH measurements, could be used to reduce or avoid "false positive" pregnancy results. These workers were not, however, concerned with self-test pregnancy tests and, in particular, were not concerned with detecting pregnancy at a very early stage.

SUMMARY OF THE INVENTION

In a first aspect, the invention provides a test device to detect pregnancy in a human female subject, the test device comprising:
an assay means to measure the absolute or relative amount of hCG in a sample from the subject;
an assay means to measure the absolute or relative amount of FSH in a sample from the subject;
and an assay means to measure the absolute or relative amount of one or more progesterone metabolites, in a sample from the subject.

The sample may be any suitable body fluid, such as whole blood, plasma, serum or urine. A urine sample is strongly preferred however as such a sample is readily obtainable and does not require an intrusive procedure to be performed. In addition, use of a urine sample facilitates self-testing by a user.

In this context, the amount of an analyte present in a sample may be determined in absolute terms (e.g. in terms of a numerical value per unit volume) or in relative terms (e.g. by reference to a predetermined threshold). In particular, the "relative amount of one or more progesterone metabolites" is not intended to mean that the concentrations of different progesterone metabolites in a sample are compared with one another, but rather that the concentration of one or more such analytes may be compared to a predetermined threshold. The assay means will be adapted and configured to measure their respective analytes although, as explained below, one assay means my be adapted and configured to measure the amount of two or more different analytes.

By way of explanation, following conception, further ovulatory cycles are unnecessary since the woman is already pregnant. Accordingly after conception folliculargenesis is inhibited by suppression of FSH production. Thus, in a pregnant woman one would expect to observe elevated levels of hCG and low levels of FSH. Accordingly, measurement of FSH can be used to help interpret the significance of the detection of slightly elevated levels of hCG, especially if it is suspected that this might be due to a non-pregnancy associated source.

By way of further explanation, during the first 10-12 weeks of pregnancy, progesterone produced by the corpus luteum supports the endometrium, thus allowing the pregnancy to continue. Progesterone level is raised during parts of the luteal phase of menstrual cycles, but this level falls back to baseline levels if pregnancy does not occur (i.e. if the subject menstruates). However if pregnancy occurs the levels of progesterone (and its urinary metabolites) will remain elevated and will continue to rise through, pregnancy, so that progesterone (and its urinary metabolites) can be used as an adjunct to hCG as an additional confirmation of pregnancy.

The test device will preferably further comprise means for interpreting the assay results to determine the outcome of the pregnancy test and, preferably, a display means to display the outcome of the test.

In a second aspect the invention, provides a method of detecting pregnancy in a human female subject, the method comprising the step of contacting a sample from the subject with a test device in accordance with the first aspect defined above. As noted above, the sample is preferably a urine sample.

The preferred features of the invention will be described in further detail below. It will be apparent that, where these are described in relation to the test device of the first aspect, they will apply equally to the method of the second aspect (and vice versa), unless the context dictates otherwise.

The test device may comprise a microfluidics-based assay, having one or more fabricated capillary channels (typically of defined bore) along which a liquid sample may flow, but more preferably the test device comprises a lateral flow assay. The test device may comprise both a microfluidic assay and a lateral flow assay. In one embodiment, the test device will comprise three lateral flow assays, with one assay for a respective one of each of the three analytes (i.e. hCG; FSH; and a progesterone metabolite).

In some embodiments it may be desirable to have more than one assay for one particular analyte. For example, one assay might be a microfluidics assay and another assay might be a lateral flow assay. Alternatively, both assays for the analyte might be microfluidics assays or might be lateral flow assays. Where both assays for an analyte are lateral flow assays, they might be on a single lateral flow test strip or on respective lateral flow test strips.

For example, hCG levels increase exponentially during early pregnancy and therefore the concentration of hCG in a urine sample from a pregnant subject may vary considerably, depending on how long the subject has been pregnant. It might be desirable therefore to provide one assay which is a relatively high sensitivity assay for hCG and one assay which is a relatively low sensitivity assay for hCG, so that the concentration of hCG in the sample can be determined over an extended concentration range. (By way of explanation, high levels of analyte can cause complications, known as the hook effect. This can lead to inaccuracies in high sensitivity assays due to a limited assay range and hence the provision of an assay with a reduced sensitivity can be beneficial, allowing accurate measurements to be made at very high analyte levels).

Normally, progesterone is not present in urine in detectable amounts. Instead it is metabolised and various progesterone metabolites are excreted in urine. The assay of the invention is therefore adapted to measure one or more progesterone metabolites in urine. Progesterone metabolites may be divided into 4 groups; pregnanediols, pregnanolones, pregnanediones, and a last group containing compounds more polar than pregnanediol. In theory, one or more metabolites from any one of those four groups may be suitable for measurement in the present invention. Preferred examples include pregnanolone (3α-hydroxy-5β-pregnan-20-one) and pregnanediol (5β-pregnane-3α-20α-diol). The latter compound is especially preferred for testing as it is the progesterone metabolite which is generally present in urine at the highest concentration (Cooke, I. D. 1976, Progesterone and its metabolites. In: Lorraine, J. A. & Bell, E. T. (eds) "Hormone Assays and their Application" pp 447-508). It will be apparent to those skilled in the art that references to e.g. pregnanediol and pregnanolone encompass, unless the context dictates otherwise, their commonly-occurring derivatives. In particular, progesterone metabolites are usually present in urine as glucuronides or, occasionally, as sulphates. Thus references herein to, for example, pregnanediol encompass in particular, pregnanediol-3-glucuronide ("P-3-G"), also sometime referred to as PdG. Further, reference herein to "progesterone" or "progesterone assay", unless the context dictates otherwise, are intended to encompass in particular progesterone metabolites and assays for progesterone metabolites respectively.

It will be appreciated that the degree of structural homology, and thus antigenic similarity, between various metabolites of progesterone can be very high. Accordingly, in an immunological-based assay, an antibody which binds to a particular progesterone metabolite with a first binding affinity, may bind to a different progesterone metabolite with a second binding affinity which may not be significantly lower than the first binding affinity, such that the antibody may cross-react to some extent. Alternatively, a highly-specific antibody could be employed which has a much higher (e.g. at least 10 fold or more) binding affinity for a particular progesterone metabolite than for other progesterone metabolites present in human urine. Accordingly, an assay for "a progesterone metabolite" may frequently detect a number of different progesterone metabolites. The degree of cross-reactivity of any reagents for different progesterone metabolites is not critical to the invention, but the person skilled in the art will appreciate that this, among other characteristics, may need to be reflected in the choice of reagent and the selection of an appropriate "threshold" value as explained below.

Similarly, there are several variants of FSH in humans which may be present in urine (e.g. fragments such as isolated β-chains), and different isoforms (see Walton W. J. et al., J Clin Endocrinol Metab., 86, 3675-85, 2001; Dahl, K. D. and Stone M. P. J Andrology, 13, 22, 1992; and Baenziger, J. U. and Green E. D Biochem. et Biophys. Acta, 947, 287-306, 1988) e.g. with varying degrees of glycosylation and an immunological-based assay may utilise an antibody which binds relatively specifically to a single variant, fragment or isoform of FSH, or may utilise a less specific antibody which binds with acceptably high affinity to several different human FSH variants. Again, this may have an impact on the choice of reagent and/or choice of a threshold value selected in the assay, but is not generally critical to the working of the invention. Similar comments apply to hCG and variants thereof.

In general terms, the concept underlying the present invention the realisation that a very high sensitivity hCG assay can be used to detect pregnancy very early, and that by additional measurement of FSH and a progesterone metabolite, the specificity of the test can be maintained at an acceptably high level (i.e. avoiding high numbers of false positive results due to the detection of hCG from non-pregnancy associated sources), without requiring knowledge of the age of the subject. The assay device is especially suitable as a simple PoC or, especially, self-test device, not requiring any medical or technical training for its use. In particular the assay device is preferably disposable after a single use. Further, the device is desirably a simple lateral flow or microfluidics-based device, in which the various assays are performed automatically once the device has been contacted with a sufficient volume of urine sample, without requiring any further user intervention. It is further preferred that the device is a digital device i.e. reads and displays the outcome of the assay to the user.

In particular the assay device of the present invention is preferably a self-test or home test device. In preferred embodiments, the assay device has an accuracy of ≥99%, even if used prior to the day of expected period. More especially, the assay device of the present invention may achieve an accuracy of ≥99% even if used as early as 2 days before the day of expected period, preferably even if used as early as 3 days before the day of expected period, preferably even if used as early as 4 days before the day of expected period, and preferably even if used as early as 5 days before the day of expected period and more preferably even if used as early as 6 day s before the day of expected period (e.g. as calculated by reference to the LH peak, or the LH surge).

Testing for hCG indicates likely positive (pregnant) results (i.e. those samples in which urinary hCG is above a predetermined threshold), which can be confirmed (or negated) by results of the FSH and progesterone metabolite assays. Thus, for example, an hCG level just above the predetermined threshold, accompanied by an elevated FSH level and a low progesterone metabolite level indicates that the subject is not pregnant (and implies that the elevated hCG level is of a non-pregnancy associated origin).

In this way, the invention provides a pregnancy test which can detect pregnancy with high sensitivity (i.e. detect 99% or more of pregnant subjects), with high specificity (i.e. 1% or lower false positive rate) and, moreover, can achieve these results even when the subjects include peri- and post-menopausal women; and even more surprisingly, at a single time point (day) at a very early stage in pregnancy (i.e. even before the day of expected period), and without any other external information (such as, e.g. the age of the subject).

Another advantage of the present invention is that it can avoid false negative results which can occur with point-of-care hCG-based pregnancy test devices when the subject has very high levels of hCG β core fragment. This problem has been recognized in the art and is described, for example, by Gronowski et al. (2009 Clinical Chemistry 55, 1389-1394). This is because an artificially low signal for hCG, caused by the inhibitory effect of excess β core fragment, will be compensated by the assay results for FSH and progesterone metabolite, which will be unaffected by the excess β-core fragment.

Advantageously, a single urine sample will be used to provide the test sample for each of the (at least) three analyte assays performed by the assay device/method of the invention. Conveniently, all three analyte assays will be performed substantially simultaneously, preferably using a single urine sample applied to the assay device. This can conveniently be accomplished by use of, inter alia, the embodiments described below.

For present purposes, the three analyte tests will be performed "substantially simultaneously" when the tests are performed using urine samples which were derived from the same episode of micturition, and the results of the assays are read within a period of 10 minutes of each other, preferably within 5 minutes of each other, more preferably within 3 minutes of each other, and most preferably within 60 seconds of each other. Desirably all three analyte tests are initiated at substantially the same time (i.e. within 60 seconds of each other) by the user applying a urine sample to a sample contacting portion of the test device.

In a preferred embodiment, the various aspects of the invention possess one or more (desirably all) of the following characteristics:
(i) a sensitivity of 99% or greater;
(ii) a specificity of 99% or greater;
(iii) the ability to achieve (i) and (ii) even if the day of testing is early in pregnancy (i.e. prior to the day of expected period, as herein defined);
(iv) the ability to achieve (i) and (ii) even when the test is performed/assay device used once, at a single time-point (i.e. on a single day);
(v) the assay device/method does not require any external information (e.g. the age of the woman or any history of the subject, such as a previous measurement of hCG, FSH or progesterone); and
(vi) the ability to achieve (i) and (ii), even when the subjects include peri- and/or post-menopausal women (as herein defined).

For the purpose of the present specification, "early" in pregnancy means prior to the day of expected period, as calculated by reference to the peak level of luteinising hormone ["LH peak"] detected in the woman occurring at or around the time of ovulation. By way of explanation, the day of expected period is usually assumed to be 15 days after the peak of LH.

The present inventors have calculated that using the apparatus and method of the invention, it should be possible to establish true pregnancy status with 99% or greater sensitivity and 99% or greater specificity, even among peri-menopausal and post-menopausal women, from an assay at a single time point.

The day of expected period can be calculated by reference to certain time points. In particular, the day of expected period can be calculated by reference to the day of LH surge (i.e. the day on which a clear marked increase in LH level is first detected in a cycle), which event usually occurs about 12-24 hours in advance of the LH peak. The day of the expected period may also be calculated by the addition of the usual cycle length (in days) to date of the last menstrual period. Other ways of calculating the expected period include the addition of 28 days to the date of the last menstrual period.

Generally speaking, the results of the analyte assays will be determined after a particular time has elapsed (usually, but not necessarily, determined by reference to the time at which the sample was contacted with a sampling region of the assay device). The time at which the analyte assay result is determined may be referred to as $t_E$. The assay result reading device may comprise some sort of integral timing means in order to determine when $t_E$ is reached. The timing means may be actuated automatically by contacting the sample with the assay device (e.g. by the liquid sample allowing a current to flow), or may be triggered by the user (e.g. depressing a switch or the like) or by any other convenient means. The assay reaction may conveniently have reached equilibrium at $t_E$ but this is not essential. $t_E$ may be reached at the same time for all of the analyte assays simultaneously, or $t_E$ may be different for the different analytes.

In some embodiments, if an analyte assay signal is still below an upper threshold value at $t_E$ the result of the assay is negative (in those formats in which it is the presence of the analyte of interest which leads to formation of the signal). The end-point of the assay may not necessarily be at completion of the reaction. Indeed, the end-point $t_E$ will normally be considered to have been reached before the reaction is complete.

The $t_E$ end point may conveniently be determined by the reader by reference to a particular time point (i.e. $t_E$ may be considered to occur a particular amount of time after commencement of the assay e.g. a particular interval after activation of the reader and/or insertion of an assay stick into the reader and/or application of the sample to the test stick). For the purposes of illustration, $t_E$ will typically occur between 1 and 10 minutes, preferably between 1 and 5 minutes after commencement of the assay.

Desirably the assay result reader will be programmed so as to repeat the test measurement if an intermediate signal is obtained. In a simple embodiment the measurement is repeated at $t_E$. Preferably however the measurement is repeated one or more times before the end point. Most preferably the reader device is programmed to repeat the measurement at regular intervals (say, for instance 1 second or 5 second intervals) until the signal exceeds the upper threshold or until $t_E$ is reached, which ever occurs first.

Inclusion of clock or other timing device in the assay result reader is desirable so that the reader can automatically take measurements at predetermined time points without further user input.

Thus, for example the reader may be programmed to take measurements at an initial time point $t_o$ and, if necessary to make repeated measurements at any desired interval (hereafter until the signal exceeds the upper threshold or $t_E$ is reached, as described above.

In addition, a clock or other timing device facilitates the reading device in determining the rate of signal accumulation. If measurements of the amount of signal are taken at two or more time points (with a known temporal separation), then the rate of signal accumulation mas readily be calculated.

It should be noted that the rate or amount of signal accumulation could be measured either in absolute terms or as a relative value (e.g. compared to a control or other comparison value, optionally obtained from a substantially contemporaneous reaction).

In particular, the assay result reader in some embodiments may determine the assay result (i.e. pregnant or not pregnant) before $t_E$ is reached if one or more analyte assay readings are well above or below (as appropriate) a particular relevant threshold level. 'Early' determination of an assay result in this way is described in EP 1484613. In the present instance, for example, if the amount of FSH in a sample is above a predetermined upper threshold (at a level where pregnancy is never observed), then the FSH assay signal will develop very quickly, and this may allow the assay result reader (or a human observer) to determine the outcome of the assay in advance of $t_E$ as a not "not pregnant" result, possibly without waiting to analyse the result of the hCG and/or progesterone metabolite assay. Similarly, if the level of progesterone metabolite in the sample is very low (e.g. below 1 μg/ml), a strong progesterone metabolite assay signal will develop very rapidly, before $t_E$ for the progesterone metabolite assay is reached, allowing an early determination of the assay result as "not pregnant", again possibly without reading the hCG assay and/or the FSH assay.

"Early" determination of the assay result may be performed before $t_E$ is reached for any of the three analytes (i.e. hCG, progesterone metabolite and FSH); or may be performed before $t_E$ is reached for any combination of two of the three analytes (i.e. hCG and progesterone; hCG and FSH; or progesterone and FSH); or before $t_E$ is reached for just one of the three analytes (i.e. at or after $t_E$ for the other two of the three analytes).

Similarly, there may be lower, middle and upper thresholds for all three analyte assays, or any one of the three analyte assays, or for any combination of two out of the three analyte assays.

The test device will comprise at least one flow path, preferably at least two flow-paths, and typically three or even four flow paths.

The term "flow-path" for the purposes of this invention refers to a substrate that is able to convey a liquid from a first position to a second position and may be for example a capillary channel, a microfluidic pathway, or a porous carrier such as a lateral flow porous carrier. The porous carrier may comprise one or a plurality of porous carrier materials which may overlap in a linear or stacked arrangement or which are fluidically connected. The porous carrier materials may be the same or different. The various assays of the test device may be provided on separate substrates or they may be provided on a common substrate such that liquid being conveyed along a flow-path of one assay is not able to cross over to the flow-path of a different assay. For example, first and second assays may be provided on the same porous carrier such that the first and second flow-paths are isolated from each other. This may be achieved for example by laser cutting parts of the porous carrier too make it non-porous, thus separating the first and second assays. Alternatively, a non-porous blocking material may be applied along a strip to provide two or more (typically essentially parallel) flow paths on the same porous carrier. In other embodiments, a single flow path may accommodate tests for two, or even three, different analytes. For example, a single flow path may include reagents for testing for hCG and may also include reagents for testing for a progesterone metabolite. Alternatively, a single flow path may include reagents so test for hCG and FSH; or a single flow path may comprise reagents to test for FSH and a progesterone metabolite. In particular, a flow path may comprise two detection zones, one for each analyte, in which a labelled reagent may tend to accumulate in a manner generally proportional (directly or inversely) to the concentration of the respective analyte in the sample.

The flow-path or flow paths in the test device may comprise a lateral flow porous carrier. Suitable materials that may be employed as a porous carrier include nitrocellulose, acetate fibre, cellulose or cellulose derivatives, polyester, polyamide, polyolefin or glass fibre. The porous carrier may comprise nitrocellulose. This has the advantage that a binding reagent can be immobilised firmly without prior chemical treatment. If the porous solid phase material comprises paper, for example, immobilisation of an antibody may be performed by chemical coupling using, for example, CNBr, carbonyldimidazole, or tresyl chloride.

The assay device/method of the present invention typically utilises one or more binding reagents. Typically the hCG assay utilises a binding reagent which binds to hCG, the FSH assay utilises a binding reagent which binds to FSH, and the progesterone metabolite assay utilises yet another binding reagent that binds to a progesterone metabolite. The assays may, in particular, comprise the use of a labelled binding reagent. As explained elsewhere, a labelled binding reagent might be used which binds to both hCG and FSH, since these two molecules have some structure in common.

For present purposes, the term "binding reagent" refers to a member of a binding pair, i.e., two different molecules wherein one of the molecules binds with the second molecule through chemical and/or physical means. The two molecules are related in the sense that their binding with each other is such that they are capable of distinguishing their binding partner from other assay constituents having similar characteristics. The members of the binding pair are referred to as ligand and receptor (antiligand), a binding pair member and binding pair partner, and the like. A molecule may also be a binding pair member for am aggregation of molecules; for example an antibody raised against an immune complex of a second antibody and its corresponding antigen may be considered to be an binding pair member for the immune complex.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein) and the like. Furthermore, specific binding pairs can include members that are analogues of the original specific binding member.

"Label" when used in the context of the labelled binding reagent, refers to any substance which is capable of producing a signal that is detectable by visual or instrumental means. Various labels suitable for use in the present invention include labels which produce signals through either chemical or physical means, such as being optically detectable Such labels include enzymes and substrates, chromogens, catalysts, fluorescent compounds, chemiluminescent compounds, electroactive species, dye molecules, radioactive labels and particle labels. Particle labels may include magnetic or electronically charged labels, which can be detected by magnetic or electrochemical means. The label may be covalently attached to the binding reagent. In particular the label may from one that is optically detectable. Preferred optically detectable labels include colloidal metallic particle labels and dye-laden particles, as below.

The label may comprise a colloidal metallic particle such as gold, silver, platinum, silver enhanced gold sol carbon sol, or carbon nanoparticles; colloidal metalloid or non-metallic particles such as tellurium or selenium; or dyed or coloured particles such as a polymer particle incorporating a dye, or a dye sol. The dye may be of any suitable colour, for example blue. The dye may be fluorescent, or comprise a quantum dot. Suitable fluorescent materials are well-known to those skilled in the art. Dye sols may be prepared from commercially-available hydrophobic dyestuffs such as Foron Blue SRP (Sandoz) and Resolin Blue BBLS (Bayer). Suitable polymer labels may be chosen from a range of synthetic polymers, such as polystyrene, polyvinyltoluene, polystyrene-acrylic acid and polyacrolein. The monomers used are normally water-insoluble, and are emulsified in aqueous surfactant so that monomer micelles are formed, which are then induced to polymerise by the addition of initiator to the emulsion. Substantially spherical polymer particles are produced. An ideal size range for such polymer particles is from about 0.05 µm to about 0.5 µm. According to an exemplary embodiment the label is a gold colloid with a preferred particle mean diameter in the range 0.02 µm to 0.25 µm.

Dried binding reagents may be provided in the flow path of a microfluidics device or on a porous carrier material provided upstream from a porous carrier material comprising a detection zone in a lateral flow type device. The upstream porous carrier material may be macroporous. The macroporous carrier material should be low or non-protein-binding, or should be easily blockable by means of reagents such as BSA or PVA, to minimise non-specific binding and to facilitate free movement of the labelled reagent after the macroporous carrier has become moistened with the liquid sample. The macroporous carrier material can be pre-treated with a surface active agent or solvent, if necessary, to render it more hydrophilic and to promote rapid uptake of the liquid sample. Further, one or more sugars (e.g. sucrose, trehalose) may be used to stabilize and help mobilise the labelled reagent. These may be applied to the flow path and/or to the porous carrier material conveniently as part of a solution in which the labelled reagent is applied to the porous carrier. Suitable materials for a macroporous carrier include plastics materials such as polyethylene and polypropylene, or other materials such as paper or glass-fibre. In the case that the labelled binding reagent is labelled with a detectable particle, the macroporous carrier may have a pore size at least ten times greater than the maximum particle size of the particle label. Larger pore sizes give better release of the labelled reagent.

The test device will conveniently comprise three or more flow paths: a respective flow path for each analyte assay. It is possible, however, that two or more analyte assays may share a common flow path (possibly in addition to an optional common sample application zone, described below). The flow path will typically comprise a capillary or other microfluidic flow channel, or one or more porous members along which an aqueous fluid, such as a urine sample, may be transported.

In one embodiment, the test device comprises three separate lateral flow assay strips, one for each analyte assay. In another embayment, the test device may comprise two lateral flow assay strips: one of the strips serving to perform an assay for one of the analytes (e.g. hCG) and the other strip serving to perform a respective assay for each of the other two analytes. One can also envisage an embodiment in which one flow path or lateral flow test strip is used to test for all three analytes.

The test device may, in particular, comprise a sample application zone. This is a zone of porous (typically bibulous) material to which an aqueous sample, such as urine, may be applied. The sample application zone may be a common zone. That is, a liquid sample applied to the common sample application zone may be transported to two or more different assay flow paths.

Typically sample is applied to the sample application zone by the user urinating directly onto the sample application zone.

In a preferred embodiment the assay device comprises a housing, which accommodates most or all of the functional components of the assays and the assay reagents. The housing is conveniently formed of a waterproof, synthetic plastics material and is preferably substantially opaque. An opacifier may be added to the plastics material in order to achieve a desired level of opacity. Suitable synthetic plastics materials for forming the housing include, in particular, polycarbonate, polystyrene, copolymers of polystyrene, polyolefins, polypropylene, polyethylene, and acrylonitrile. The housing may desirably be formed in two or more parts, which are joined together with the majority (or all) of the rest of the assay device components accommodated within or between the assembled parts of the housing. The parts of the housing may be joined and fastened by conventional fastening means, such as a snap fit action, or by plastic welding or the like.

In a preferred embodiment, the assay device comprises a housing, (typically having the features noted above), and wherein a sample application portion or zone extends beyond the housing, to facilitate application of a urine sample to the sample application portion or zone. The sample application portion or zone which extends beyond the housing may be covered, prior to use, by a removable cap. The cap may also preferably be formed of a synthetic plastics material which may be opaque, or transparent or translucent. Typically the cap is replaced once sample has been applied to the sample application zone.

AN absorbent "sink" can be provided at a distal, downstream end of the assay flow-paths. A common sink may be provided or a sink may be provided at the distal end of each assay. The absorbent sink may preferably comprise a highly absorbent material such as, for example, CF7 Whatman paper, and should provide sufficient absorptive capacity to remove any unbound label from the vicinity of the detection zone. As an alternative to such a sink it can be sufficient to have a length of porous solid phase material which extends beyond the detection zone. An advantage of providing a highly absorbent sink is that it removes or substantially removes excess labelled binding reagent from the flow-paths of the respective assays. This has the effect of minimising the extent of unbound labelled binding reagent in the vicinity of respective zones and therefore enables assay flow paths to be employed in the device that may have differing amounts of labelled binding reagent.

The test device will conveniently comprise other features known to those skilled in the art and commonplace in conventional self-test or home test pregnancy testing devices, including (but not limited to), sample sufficiency indicator (e.g. as described in PCT/EP2013/061178), an "anti-flood" pad (e.g. as disclosed in WO2012/069610), using flow of sample as an assay control (e.g. as disclosed in EP 1,484,611; U.S. Pat. No. 6,194,222); "early" determination of positive or negative results (e.g. as disclosed in EP 1,484,613; U.S. Pat. No. 5,679,584); automatic "wake up" of electronic devices (e.g. automatic actuation upon wetting of the device by sample, which completes an electrical circuit); and use of a digital assay progress meter (e.g. as in European Community Design Registration No. 1367304) or a "colour change wick" or the like which gives a visual indication to a user when sample has been applied to the test device and/or a visual indication that the assay has commenced (e.g. WO 2003/058245). The test device will advantageously be presented to the consumer in waterproof packaging, the packaging optionally further comprising a desiccant, such as a sachet of silica gel.

The assay will conveniently be supported on some sort of support or backing layer to provide mechanical strength and a suitable degree of rigidity. The assay(s) plus support may conveniently be referred to, and provided, as a test stick. All three assays may be on a single stick, or on two, three or even four (i.e. more than one stick for one analyte) test sticks. The test stick or sticks may be adapted and configured to be inserted by the user into the test device, or the test stick or sticks may, more preferable, form an integral part of the test device which is purchased by a consumer with the test stick(s) pre-inserted or loaded in the test device.

The results of the assays may be read by an extrinsic assay result reading means, or directly by a user but, far more preferably, the test device will comprise an integral assay result reader for reading the result of an assay. The assay result reader preferably reads the results of all three analyte assays. The assay result reader will advantageously comprise an electronic component, especially a digital electronic component, such as a microprocessor. Typically (but not necessarily) the assays are read by optical means i.e. measuring the amount of light reflected and/or transmitted by a detection zone, in which an optically labelled reagent tends to accumulate in a manner proportional (directly or inversely) to the concentration of analyte in the sample. Alternatively the assays may be read by, for example, magnetic or electrochemical measurement. Obviously, the way in which the assay is read may depend on the properties of the label(s) used to label the assay reagent(s).

An extrinsic assay result reading means may comprise a dedicated result reading device (e.g. similar to that described in EP 1066530). Alternatively, the extrinsic assay result reader may be "non-dedicated", such as a mobile phone or other portable electronic device (e.g. a tablet computer), preferably provided with a camera, where the assay result is read by mediating the signal intensity generated by a visible label.

The assay result reader, whether extrinsic or forming part of an integrated assay device/assay result reader, may read and interpret the assay results, or may transmit assay result data to a remotely-located device for the assay data to be interpreted. The assay data may be transmitted to the remotely-located device in real time. The data may be transmitted via an internet connection, or may be stored on a memory device (such as a 'flash' drive or the like) which is physically transported to the remote device, or the data may be transmitted by wireless communication means (e.g. Bluetooth, near field communication [NFC], or the like).

A microprocessor may control the operation of the optical reading or other assay reading components, and will conveniently be programmed with, or fee able to access, relevant assay signal threshold values for each of the analytes, compare the actual assay signal values with the predetermined thresholds, and interpret the assay results so as to determine the outcome of the pregnancy test.

The assay result reader thus comprises the necessary components for reading the result of the assays. The test device will advantageously also comprise an assay result display, for displaying the outcome of the pregnancy test to a user. Typically the display will comprise an LCD, hot other types of display are possible (e.g. using "electronic inks"). In those embodiments in which the assay device (or, more specifically, a component thereof) requires a power source to operate, then the assay device will preferably be provided with an integral power source, such as a battery. Very small, and cheap, batteries are commercially readily available. The device may also be provided with a switch to connect the integral power source and activate the device.

In alternative embodiments, the results of the assays may be directly read by a user, in the manner known from conventional "self-test" pregnancy tests e.g. by a user inspecting one or more windows overlying the assay detection zones to determine the presence or absence of a detectable signal at one or more (or all) of the detection zones. Each detection zone may be provided with a separate window in an opaque housing to allow a user to inspect the detection zone. Alternatively, a large window may accommodate two or more (or all) of the detection zones. Typically, in such user-read devices, the user will directly inspect the detection zones of the lateral flow or microfluidics assays. In other formats a user may determine the result by reference to a colour chart or indicator. Conveniently, the test device will be provided together with instructions or guidance for reading the assay result (if the device does not interpret the assay results for the user). For example, the user may be provided with a printed colour chart to facilitate interpretation of such directly-read visual tests.

A combined pregnancy test stick/assay result reader device with display may be referred to as a "digital pregnancy test", and such digital test devices are commercially available and could be adapted, with the benefit of the present disclosure, to provide a test device in accordance with the present invention.

The microprocessor will desirably be programmed so as to cause the assay result reading components to read the results of the assay(s); interpret the assay results; and display the conclusion to the user.

The components for reading the results of the assays will preferably comprise at least one light source, and at least one photodetector. The at least one light source is preferably a light emitting diode (LED). The at least one photodetector is preferably a photodiode or a phototransistor. The light source illuminates a detection zone on the assay, which zone tends to accumulate a labelled substance during performance of the assay, in a manner which depends on the concentration of the analyte of interest in the sample applied to the assay. The labelled substance may accumulate in a way which is positively correlated with the concentration of the analyte (i.e. the greater the concentration of analyte, the greater the amount of label which accumulates in the detection zone). Typically a sandwich assay format is employed, which is well-known to those skilled in the art. Alternatively, the accumulation of the labelled substance may be negatively correlated with the concentration of the analyte (i.e. the greater the concentration of the analyte, the less the amount of label which accumulates in the detection zone). Such, a negative correlation is typical of a competition or inhibition-type assay, which type of assay is often employed when the analyte of interest is a hapten and/or is too small to accommodate simultaneous binding of two different antibodies (e.g. as in the case of progesterone metabolites). FSH and hCG are both hetero-dimeric molecules, comprising α and β subunits. The α-subunit of FSH and hCG is essentially identical, such that antibodies directed to the α subunit may bind to both FSH and hCG. An assay for these two molecules may potentially therefore utilise a common reagent which may be, for example, a mobilisable, directly labelled (i.e. optically detectable) antibody. Respective detection zones may comprise an immobilised capture antibody, which is specific for the β subunit (which differs between FSH and hCG). Obviously, this relates to a sandwich type immunological assay, but other assay formats are well-known and could be used instead.

It is possible that, if a sample contains high levels of hCG (e.g. because the sample is provided by a subject in whom a pregnancy is relatively advanced) then, an antibody specific for the common a subunit antibody might be 'swamped' by the high levels of hCG, effectively reducing the amount of antibody available for binding to FSH and possibly thereby causing an underestimation of the amount of FSH present in the sample. In practice this is probably unlikely to cause any problem, because such high levels of hCG would nearly always (>99.9%) be due to pregnancy, which would be correctly detected and interpreted by the test device. Irrespective of any FSH assay result. It is also possible to use a double β subunit specific antibody pair for the hCG assay and a double β specific antibody pair for the FSH assay. This format would negate the above effect seen at high analyte levels.

In view of the need to minimise cost, (especially in those embodiments in which the device is disposed of alter a single use), it is preferred it to use a single photodetector to detect light emanating from the detection zone of at least two, preferably three, different assays. It will be appreciated that the light does not truly originate from the detection zones—it originates from the light sources,—but it is reflected by and/or transmitted through, as the case may be, the detection zones such that it appears to emanate therefrom. Typically, but not necessarily, each detection zone is illuminated by a respective light source, such as an LED.

A single light source, such as an LED, could be used to illuminate the detection zone of at least two different assays and if possible, three different assays. However, it is also possible to provide a plurality of LEDs. For example, one LED may be provided to illuminate each respective detection zone. Where a plurality of LEDs is provided, these may produce the same colour illumination, or may produce illumination of different wavelengths. There may be embodiments in which the number of LEDs for other light sources) equals, or even exceeds, the number of detection zones. Alternatively, different geometries can be used in which one LED illuminates two detection zones, such that the number of LEDs is less than the number of detection zones.

The device may typically utilize a reference zone—this is a portion of a microfluidics or lateral flow assay flow path which is used to reference a reading obtained from a detection zone. The use of a reference zone is well known to those skilled in the art. In particular, the device may utilize a 'shared' reference zone (as disclosed in EP 2,031,376) in which one reference zone is used as a reference for two or more detection zones, at least one of which is located on a different flow path.

The microprocessor or computerised control may cause the light source(s) to illuminate the one or more detection zones sequentially, so as to distinguish light reflected by and/or transmitted through the respective detection zones. In one embodiment, light sources emit light of different wavelengths at different times, and the photodetector(s) distinguish the different wavelengths. Additionally, or alternatively, optical baffles (fixed or adjustable) may be used to control the area illuminated by a particular light source. More details of the sort of optical arrangements that can be used are disclosed in, e.g. EP 1,484,601, U.S. Pat. Nos. 6,055,060 and 5,889,585. For the avoidance of doubt, the term "light" as used herein is not intended to refer solely to radiation in that part of the electromagnetic spectrum which is visible to a human observer and encompasses, for example, ultra violet and infra-red radiation. Nevertheless, operation of the components in, and sensitivity to, the visible part of the spectrum may be preferred.

The microprocessor or computerised control means will preferably comprise a number of stored analyte threshold values, against which the assay results are compared, to allow the assay result reading device to interpret the results and display an appropriate conclusion (e.g. pregnant or not pregnant) to a user. The microprocessor or control means will advantageously be programmed with an algorithm to measure the test results, compare them with the predetermined thresholds, and display the conclusion.

In one embodiment, the microprocessor or control means will first determine the hCG assay result, and compare that with a predetermined lower hCG threshold. If the determined hCG assay result is below the predetermined lower hCG threshold, it can immediately be ascertained that the subject is not pregnant, and this result indicated to the user by the display (e.g. by forming the words NOT PREGNANT, or their equivalent in any language; or by means of an intuitive symbol e.g. a minus sign or a zero).

If however the measured hCG assay result is above the predetermined lower threshold, the assay result reader may proceed to measure the result of the FSH assay. If the FSH assay result indicates that the FSH concentration in the sample is greater than it's the predetermined threshold, it can be ascertained that the subject is not pregnant and this displayed to the user as described above.

If however the measured FSH level in the sample is below its respective predetermined threshold, the assay result reader may then measure the result of the progesterone metabolite assay (in this instance, an assay for P3G). If the assay result indicates that the concentration of P3G in the sample is below its respective predetermined threshold, it can be ascertained that the subject is not pregnant. If the P3G concentration in the sample is above the predetermined threshold, the subject is pregnant, and the assay result reader will display the appropriate conclusion to the user via the display.

The threshold values may be stored in the device of the invention as absolute analyte concentrations (i.e. in terms of mass or IU per unit volume) and/or as absorbance values, or in any other convenient manner.

In one embodiment the device may be provided with an upper and a lower threshold for one, two or all three of the hCG/FSH/progesterone analytes. For example, in one embodiment the device may have an upper hCG threshold and a lower hCG threshold. If the measured hCG concentration exceeds the upper hCG threshold, the device may declare that the subject is pregnant without analyzing the results of the FSH/progesterone assays. Such a declaration may be made by the device "early" (e.g. before the assay has reached an equilibrium), if it is apparent that the hCG analyte assay result will exceed the upper threshold. In other embodiments, the 'Pregnant' result is still confirmed by checking the results of the FSH and progesterone assays.

If the hCG assay result is below the lower hCG threshold, then the device declares that the subject is not pregnant (with or without confirmation by the FSH and progesterone assay results). If the hCG assay result is above the lower hCG threshold, but does not exceed the upper hCG threshold, then the device will require the FSH and progesterone assay results in order to arrive at a determination of pregnancy or non-pregnancy. The device may inspect those FSH and progesterone assay results sequentially (e.g. first one analyte, then the other, in either order) or in parallel.

In particular the device may have an upper or lower threshold for the FSH and/or progesterone assays. It may be that the choice of which of a plurality of thresholds to apply in a particular instance will depend on the absolute or relative concentration of analyte detected in the other two assays, such that a "weighting" or "compensation" scheme may be employed. For example, an hCG concentration which is determined to be at the higher end of the intermediate range between the upper and lower hCG thresholds might "compensate" for a relatively low progesterone concentration, by causing the device to apply a lower progesterone threshold in arriving at a pregnant/not pregnant determination. Conversely, low FSH and/or high progesterone, for example, might compensate for a relatively low hCG concentration in the sample.

The measurement of the assay sad/or interpretation of the assay result may comprise one or more data processing steps, in which assay data are subjected to one or more computations or other type of processing. Such processing will conveniently be performed by a digital electronic device such as a microprocessor or the like, which will typically form part of an extrinsic, or an integral, assay result reader. For example the data processing may comprise the calculation of a ratio. In particular, the processing step can comprise the calculation of the ratio of FSH: progesterone metabolite or vice versa. The ratio may be based on relative signal intensities or on calculations of the concentration of the respective analytes derived from the measured signal intensities, or other suitable relevant parameter. More especially a 'borderline' hCG signal intensity or derived hCG concentration, may be verified or checked by calculation of an FSH: progesterone metabolite (or vice versa) ratio.

Further, the device may assay other analytes, in addition to hCG, FSH and progesterone. These other analytes might include, in particular, hormones such as for instance LH, hPL (human Placental Lactogen) and/or Relaxin and/or estrogen or a metabolite thereof. Another example of such a hormone is thyroid stimulating hormone (TSH). TSH is related to hCG, FSH (and LH) in that all of these hormones comprise an α subunit which is very closely similar to the α subunit of the other hormones. TSH also comprises a β subunit which is unique to TSH. TSH levels in urine have been measured previously (see e.g. Yoshida et al., 1988 Endocrinol, Jpn. 35, 733-739), although the concentration is rather low. The concentration of such one or more additional analytes may also be taken into account by the device in arriving at a pregnant/not pregnant determination, possibly by influencing the choice of applicable threshold values for one or more of the hCG/FSH/progesterone analytes. A ratio of the one or more further analytes to one or more of hCG, FSH and progesterone may be measured. In particular, a ratio of TSH to hCG (or vice versa) may be measured. The measurement of other analytes may be especially useful in the refinements of the invention described below.

In a refinement of the basic principles described above, it may be desired not only to indicate to a user whether the subject is pregnant or not, but also (if pregnant) the extent of the pregnancy (i.e. gestational age) in terms of the approximate amount of time elapsed since conception. This could be indicated by showing a number of days or, more preferably a number of weeks. Conveniently one of three intervals might be display: 1-2 weeks; 2-3 weeks; and >3 weeks. In order to facilitate this, the test device may advantageously be provided with a plurality of different hCG concentration thresholds (or, more accurately, hCG assay test result thresholds) which correspond to respective numbers of weeks since conception. Methods of achieving this is disclosed in WO 2009/147437. Again, in order to facilitate this embodiment, it may be desirable for the test device to be able to test the hCG concentration over an extended range (e.g. by including both a relatively high sensitivity test and a relatively low sensitivity test for hCG), and suitable methods of achieving this are described in WO2008/122796. Estimation of gestational age of the pregnancy may be facilitated by measuring the concentration of other analytes in addition to hCG e.g. hPL (see WO2012/055355), and/or progesterone metabolite(s).

In some embodiments it will be desirable for the test device also to comprise some sort of control function. This is conventional in self-test devices to provide some indication that the test has functioned correctly.

Typically a control function will comprise the use of a control zone, in which a labelled reagent will tend to accumulate if enough sample has been applied to the sample application zone of the test device. Conventionally the labelled reagent will be a labelled antibody or other reagent which is releasably deposited in dried form at an upstream or proximal portion of a test strip and is mobilized upon rehydration by the sample, and captured by a specific capture agent immobilized in the control zone. The control indicates whether enough sample has been applied to the test device and indicates that the test reagents have retained their binding properties to a reasonable extent, and that the label reagent has been mobilized to a sufficient extent.

In embodiments, the invention relates to a test device configured to determine, in a sample, the presence and/or amount of each of a first marker, a second marker, and a third marker.

The sample is a sample obtained from a female mammal, e.g., a female human. The sample is typically a liquid sample, e.g., a urine sample or a blood based sample, such as whole blood, serum, or plasma.

The first marker is a marker indicative of the presence of an embryo in the female, e.g., hCG, or a metabolite of such marker. Examples of hCG metabolites include nicked intact hCG, free beta hCG, nicked free beta hCG, free alpha hCG, betacore fragment. Other examples, of markers indicative of the presence of an embryo include markers that can be differentiated from being of maternal origin (e.g. a marker made essentially only by the embryo (e.g. HPL)), a marker produced in a different form to the same marker as secreted by the mother (e.g., hyperglycosylated hCG as compared to pituitary hCG), a marker present at an increased amount in maternal circulation in the presence of an embryo as compared to the in the absence of the embryo (Placental Growth Factor (PlGF), endoglin, (soluble fms-like tyrosine kinase (sFlt), Vascular Endothelial Growth Factor (VEGF), AFP (Alpha fetoprotein)).

The second marker is a marker indicative of follicular-genesis or other follicular growth or activity in the female, e.g., FSH, LH or inhibin B, or a metabolite of such markers. Examples of FSH and its metabolites include free beta FSH and products of proteolytic degradation.

The third marker is a marker indicative of a maternal factor secreted or produced in connection with the maintenance of a pregnancy of the female, e.g., progesterone, or a metabolite of such marker e.g., P3G. Other such markers include either endometrial growth factors, forms of estrogen e.g. unconjugated estriol/estradiol and breakdown forms of progesterone-induced binding protein.

Each of the first, second, and third markers may be different from each of the other markers. Each of the first, second, and third markers include isoforms thereof, e.g., isoforms which differ in their glycosylation patterns resulting in more acidic or basic forms.

The test device may be configured to determine the presence of pregnancy if the amount of the first marker exceeds a first threshold. The determination of the presence of pregnancy may be made without use of or reference to the presence or amount of at least one of the second marker and the third marker in the sample obtained from the female. The determination of the presence of pregnancy may be made without use of or reference to the prescence or amount of the second marker, the third marker, or any combination thereof in the sample obtained from the female. The first threshold may be determined prior to use of the test device. For example, the first threshold may be determined as the time of manufacture of the test device. The first threshold may be determined without use of or reference to the presence or amount of at least one of the second marker and the third marker in the sample obtained from the female. The first threshold may be determined without use of or reference to the presence or amount of the second marker, the third marker, or any combination thereof in the sample obtained from the female. In an exemplary embodiment, the test device is configured to determine the presence of pregnancy if the amount of the first marker exceeds a first threshold, the first threshold is determined prior to use of the device and each of the determination of first threshold and the determination of pregnancy is made without use of or reference to the presence or amount of the second marker, the third marker or any combination thereof in the sample obtained from the female.

The test device may be configured to determine the absence of pregnancy if the amount of the first marker falls below a second threshold (or is absent). The determination of the absence of pregnancy may be made without use of or reference to the presence or amount of at least one of the second marker and the third marker in the sample obtained from the female. The determination of the absence of pregnancy may be made without use of or reference to the presence or amount of the second marker, the third marker, or any combination thereof in the sample obtained from the female. The second threshold may be determined prior to use of the test device. For example, the second threshold may be determined at the time of manufacture of the test device. The second threshold may be determined without use of or reference to the presence or amount of at least one of the second marker and the third marker in the sample obtained from the female. The second threshold may be determined without use of or reference to the presence or amount of the second marker, the third marker, or any combination thereof in the sample obtained from the female. In an exemplary embodiment, the test device is configured to determine the absence of pregnancy if the amount of the first marker falls below the second threshold (or is absent), the second threshold is determined prior to use of the device and each of the determination of the second threshold and the determination of the absence of pregnancy is made without use of or reference to the presence or amount of the second marker, the third marker or any combination thereof in the sample obtained from the female.

In embodiments, the test device is configured to determine the presence or absence of pregnancy further based on the second and third markers if the amount of the first marker (i) is equal to or greater than the second threshold and/or (ii) is equal to or less than the first threshold. The test device may be configured to determine the presence or absence of pregnancy further based on the second and third markers only if the amount of the first marker (i) is equal to or greater than the second threshold and/or (ii) is equal to or less than the first threshold. The test device may be configured to determine the presence or absence of pregnancy further based on the second and third markers only if the amount of the first marker (i) is equal to or greater than the second threshold and (ii) is equal to or less than the first threshold.

For example, the test device may be configured (1) (a) if the amount of the first marker exceeds the first threshold, determine the presence of pregnancy and do so without use of or reference to the presence or amount of the second marker and/or the third marker and/or (b) if the first marker falls below the second threshold determine the absence of pregnancy and do so without use of or reference to the presence of amount of the second marker and/or the third marker and (2) if the amount of the first marker is (i) equal to or greater than the second threshold and/or (ii) equal to or less than the first threshold determine the presence or absence of pregnancy and do so only further based on the second and third markers.

In embodiments, the test device is configured (1) (a) if the amount of the first marker exceeds the first threshold, to determine the presence of pregnancy and do so without use of or reference to the presence or amount of the second marker and/or the third marker and/or (b) if the first marker falls below the second threshold to determine the absence of pregnancy and do so without use of or reference to the presence or amount of the second marker and or the third marker and (2) if the amount of the first marker is (i) equal to or greater than the second threshold and (ii) equal to or less than the first threshold (A) to determine the presence of pregnancy only if (x) the second marker is absent or the amount of the second marker falls below a third threshold and (y) the amount of the third marker exceeds a fourth threshold. Under clause (2) of the embodiment set forth in the previous sentence, if either (x) the amount of the second marker exceeds the third threshold or (y) the amount of the third marker falls below the fourth threshold, the test device determines the absence of pregnancy.

In an exemplary embodiment the test device is configured (1) (a) if the amount of the first marker exceeds the first threshold, to determine the presence of pregnancy and do so without use of or reference to the presence or amount of the second marker, the third marker or any combination thereof and (b) if the first marker falls below the second threshold to determine the absence of pregnancy and do so without use of or reference to the presence or amount of the second marker, the third marker or any combination thereof and (2) if the amount of the first marker is (i) equal to or greater than the second threshold and (ii) equal to or less than the first threshold (A) to determine the presence of pregnancy only if (x) the second marker is absent or the amount of the second marker falls below a third threshold and (y) the amount of the third marker exceeds a fourth threshold. Under clause (2) of the embodiment set forth in the previous sentence, it either (x) the amount of the second marker exceeds the third threshold or (y) the amount of the third marker falls below the fourth threshold, the test device determines the absence of pregnancy. The second threshold is lower than the first threshold. For example, the second threshold may be at least about a 5 mIU/ml, at least about 7.5 mIU/ml, at least about 10 mIU/ml, or at least about 12.5 mIU/ml lower than the first threshold. The first threshold may be about 25 mIU/ml or less, about 20 mIU/ml or less, about 15 mIU/ml or less, or about 12.5 mIU/ml or less. The second threshold may be at least about 1.5 mIU/ml or greater, about 2 mIU/ml or greater, about 2.5 mIU/ml or greater, or about 5 mIU/ml or greater. As discussed herein, in embodiments, the first marker is hCG and the first and second thresholds are applicable to the amount of hCG. As discussed herein, in embodiments, the third threshold is applicable to the determination of FSH or a metabolite thereof. The third threshold may be at least about 6 mIU/ml, least about 7 mIU/ml, at least about 8 mIU/ml, at least about 9 mIU/ml, at least about 10 mIU/ml, at least about 11 mIU/ml, at least about 12 mIU/ml. The third threshold may be about 15 mIU/ml or less, about 14 mIU/ml or less, about 13 mIU/ml or less, about 12 mIU/ml or less, about 11 or less, or about 10 mIU/ml or less. As discussed herein, in embodiments, fourth threshold is applicable to P3G or a metabolite thereof. The fourth threshold may be at least about 6 ug/ml, at least about 7 ug/ml, at least about 8 ug/ml, at least about 9 ug/ml, at least about 10, at least about 11 ug/ml, at least about 12 ug/ml, or at least about 13 ug/ml or less. The fourth threshold may be about 15 ug/ml or less, about 14 ug/ml or less, about 13 ug/ml or less, about 12 ug/ml or less, about 11 ug/ml or less, or about 10 ug/ml or less.

A determination of the presence of a marker may include a determination that the marker is absent. The determined amount of a marker may be an absolute amount, e.g., an amount of the marker per unit volume of sample, a relative amount, e.g., an amount of the marker relative to an amount of a marker of kidney function, e.g., creatinine, and/or an amount of the marker relative to an amount of a marker other than either of the other of the first, second, or third markers. For example, the amount of any or all of the first marker, second marker, or third marker may be determined relative to an amount of another marker such as another, different hormone.

BRIEF DESCRIPTION OF THE SEVERAL VIEWS OF THE DRAWINGS(S)

The various features of the invention will now be further described by way of illustrative example and by reference to the accompanying drawings, in which.

EXAMPLES

Example 1

In initial experiments, urinary hCG, urinary FSH & urinary P3G were measured in 119 non-pregnant volunteers in a peri & post-menopausal (PP, age 41-90) cohort of which a total of 50 samples had [hCG]≥2.5 mIU/ml and from 72 pregnant volunteers who carried pregnancy successfully to term (age 21-40) from Day-7 EMP (expected missed period) to Day +3 BMP. Samples were tested where available leading to a total of 589 early pregnancy samples ("EPS"), of which 434 had [hCG]≥2.5 mIU/ml, as evaluated by a PerkinElmer® Delfia® assay.

Analysis of these results showed that, using a urinary hCG threshold level of at least 2.5 mIU/ml to define pregnancy coupled with both a FSH threshold of 10 mIU/ml or less and a P3G threshold of at least 4 µg/ml, a true pregnancy could be called with 100% positive prediction (no false positives in the non-pregnant cohort). The threshold levels of the three analytes used to define pregnancy, as established by this study, might change with a bigger dataset, but the results show that by using hCG in combination with FSH & P3G, pregnancy-derived hCG could be differentiated from pituitary derived peri- and postmenopausal hCG.

The results, using these thresholds, are presented in Table 1 below.

| Group A | | |
|---|---|---|
| Peri/Post-Menopausal (PP) (n = 119) | [hCG] ≥2.5 mIU/ml (n = 50) | [FSH] ≥10 mIU/ml & [P3G] <4 µg/ml |
| 41-45 years old (n = 5) | n = 1 | No False +ves |
| 45-50 years old (n = 16) | n = 4 | No False +ves |
| 50-55 years old (n = 25) | n = 5 | No False +ves |
| >55 years old (n = 73) | n = 40 | No False +ves |
| Group B | | |
| Early Pregnancy Samples (n = 589) | [hCG] ≥2.5 mIU/ml (n = 434) | [FSH] <10 mIU/ml & [P3G] ≥4 µg/ml |
| SUMMARY: | | |
| Cut-off 2.5 mIU/ml hCG | Cut-off 10mIU/ml FSH & 4 µg/ml P3G | 100% Positive Prediction |

The results is Table 1 are very significant. They show that in group A, a very sensitive hCG test (detecting as little as 2.5 mIU/ml of hCG), when combined with tests for FSH and a progesterone metabolite (P3G), gave a zero false positive rate in a statistically significant sample of women, whilst successfully identifying all pregnant subjects in Group B.

Example 2

In one embodiment of the invention, a pregnancy test device would comprise a lateral flow immunoassay constructed in a two strip nitrocellulose (NC) format, with an hCG sandwich assay formatted onto a first strip. A FSH sandwich assay and a competitive P3G assay would be formatted on a second separate strip with two distinct capture zones. Both strips would run simultaneously via a common sample application zone contacting a porous medium which would contact both nitrocellulose strips. The device would digitally measure the signal response (bound label) on the NC capture zones in response to the amount of analyte of interest. An in-built algorithm would give a digitally displayed response on the screen to the end-user (Pregnant/Non-Pregnant and/or a gestational age) depending on the levels of analytes.

Figure 6:
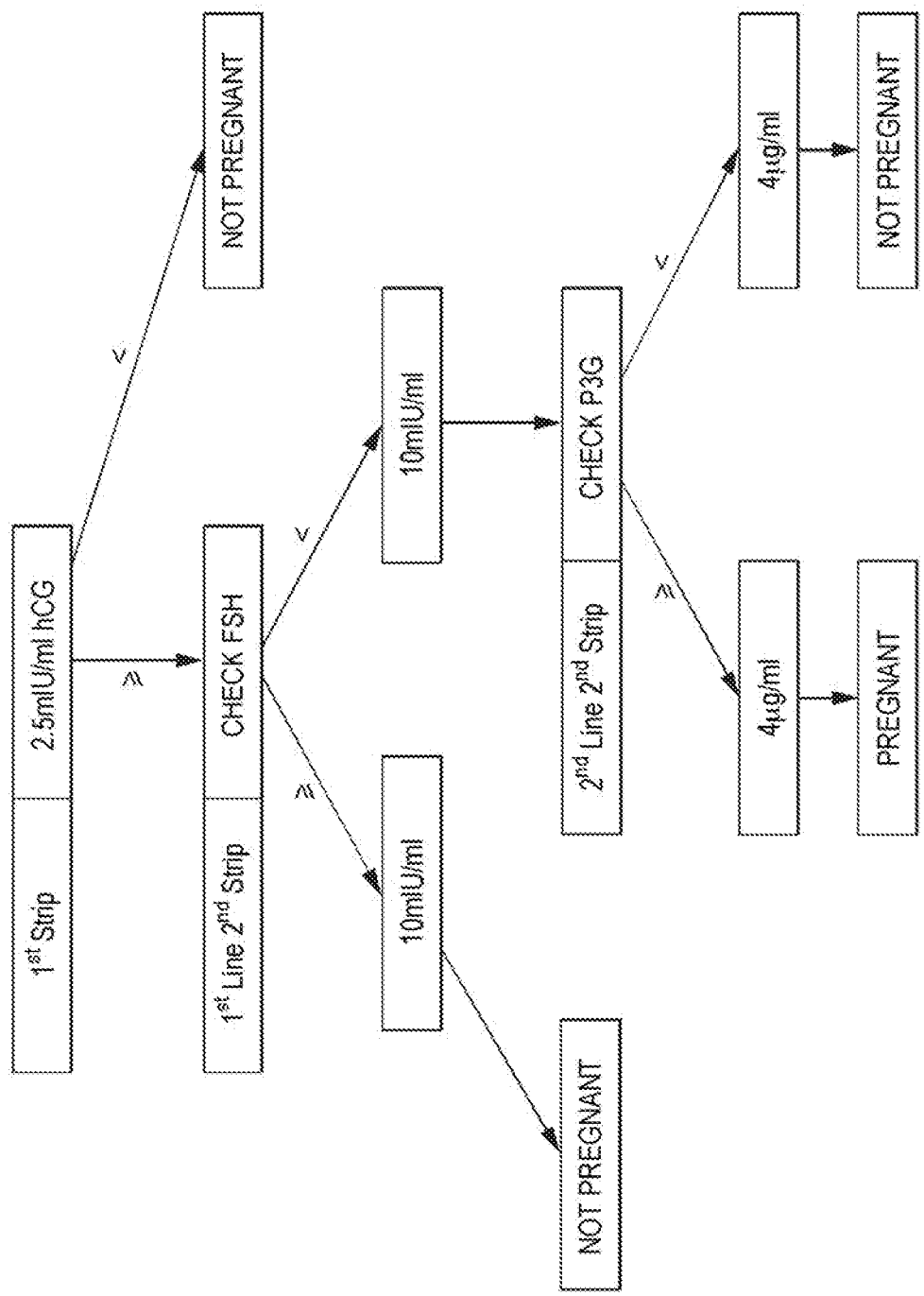
FIG. 6 illustrates schematically one embodiment of an algorithm/logic tree of use in a device in accordance with the invention.

An example of a possible algorithm is illustrated schematically in FIG. 6. It should be noted that the algorithm presented in FIG. 6 is only one embodiment and many other embodiments could be used. It should also be noted that the absolute analyte concentrations presented in FIG. 6 are purely illustrative, and other analyte thresholds might be employed.

Example 3

Figure 1:
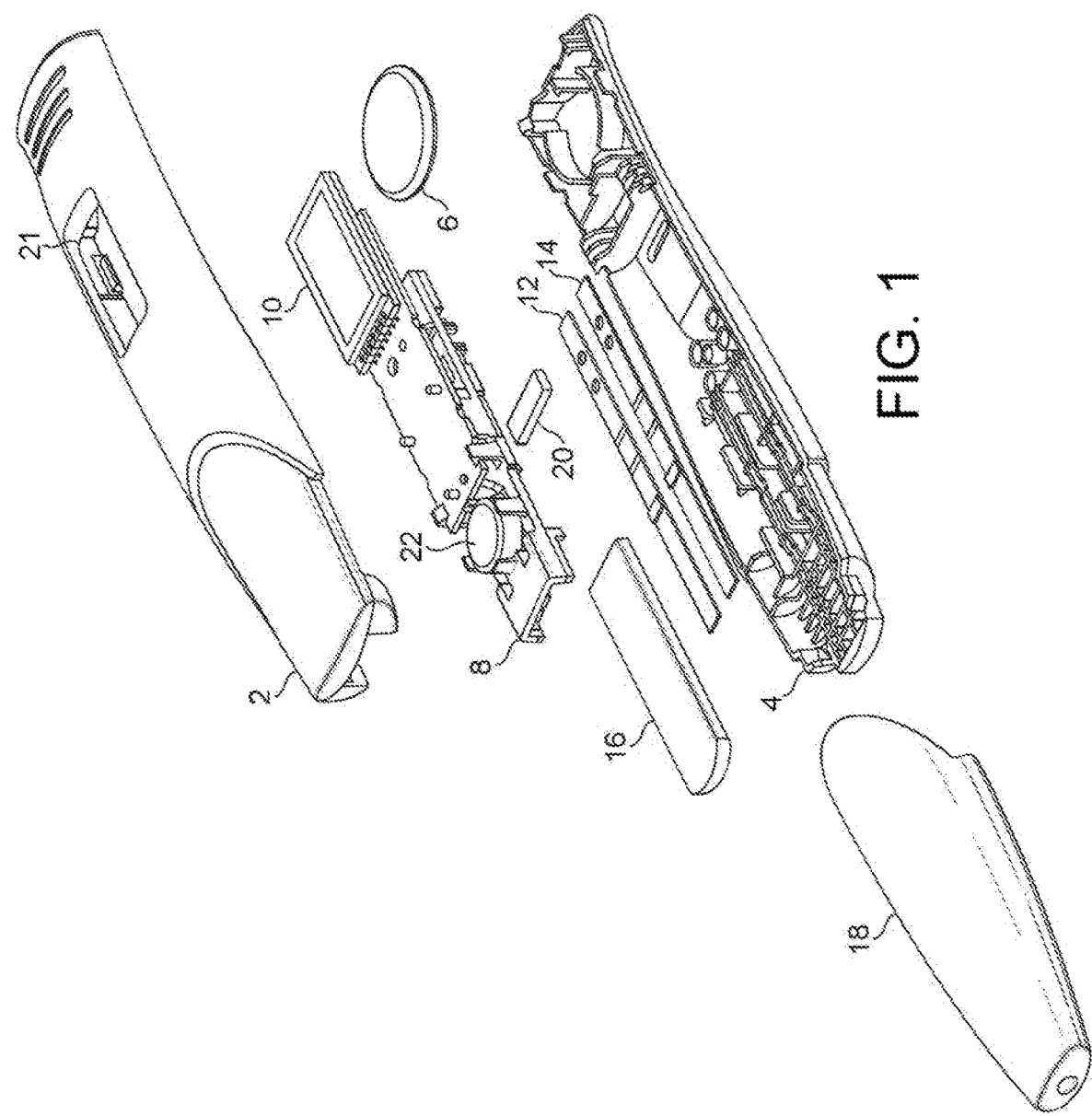
FIG. 1 is an exploded view of one embodiment of a device in accordance with the invention.

Referring to FIG. 1, which shows an exploded view of one embodiment, a device in accordance with the present application comprises a two-part housing, formed of synthetic plastics material. The housing has a top part 2 and a bottom part 4. The housing is formed of an opaque plastics material such as polycarbonate or polypropylene. If necessary an opacifier may be included.

Within the housing is a power source, such as small button cell 6 which delivers electrical power to the components mounted on a printed circuit board assembly (PCBA), 8. These include, in particular, one or more LEDs and photodiodes and a liquid crystal display 10. The components mounted on the PCBA 8 include those necessary to read the results of assays performed on the two lateral flow assay strips mounted within the housing. One of the strips 12 is for performing an hCG assay, and the other strip 14 is for performing both an FSH and a pregnanediol-3-glucuronide, (P3G) assay.

The top and bottom parts 2, 4 of the housing co-operate to form a substantially moisture-impermeable seal around the aforementioned components. A urine sample reaches the lateral flow assay strips 12, 14 by means of a sampling wick 16. One end region of the sampling wick 16 is in liquid flow communication with an adjacent end region of each of the assay strips 12, 14 (such that the sampling wick acts as a common sample application zone).

An opposed end region of the sampling wick 16 projects through and beyond an aperture in one end of the housing, allowing sample to be applied to the sampling wick. The projecting portion of the sampling wick is protected by a removable cap 18, which is shaped and dimensioned so as to co-operate with an end of the housing to be received thereby and form a snug, close-fitting engagement therewith.

In the illustrated embodiment, to apply a urine sample to the sampling wick 16, the user removes the cap 18 and urinates directly onto the wick. The wick is made of absorbent material and so the sample is absorbed into the wick and flows by passive means along the wick and into the assay strips 12, 14. The user then, optionally, replaces the cap 18. In order to assist the flow of sample into and along the assay strips, the assay strips are in liquid flow communication at their distal end (i.e. the end further from the sampling wick 16) with a "sink" pad 20 of highly absorbent material.

The lateral flow assays proceed in conventional manner, resulting in the accumulation of a labelled binding reagent, in an analyte concentration-dependent manner (proportional or inversely proportional as the case may be) at a detection zone(s) on the test strips 12, 14, which is detected and read by the assay reading components mounted on the PCBA 8. A microprocessor ASIC or the like analyses and interprets the readings and displays the assay result on the LCD 10 which is visible to the user via a window or aperture 21 formed at a suitable location in the top part 2 of the housing.

It is important that prior to use, the lateral flow test strips 12, 14 are kept dry, and for this reason the PCBA is provided with a receptable for a desiccant 22, which absorbs moisture from the interior of the housing.

Example 4

Figure 2:
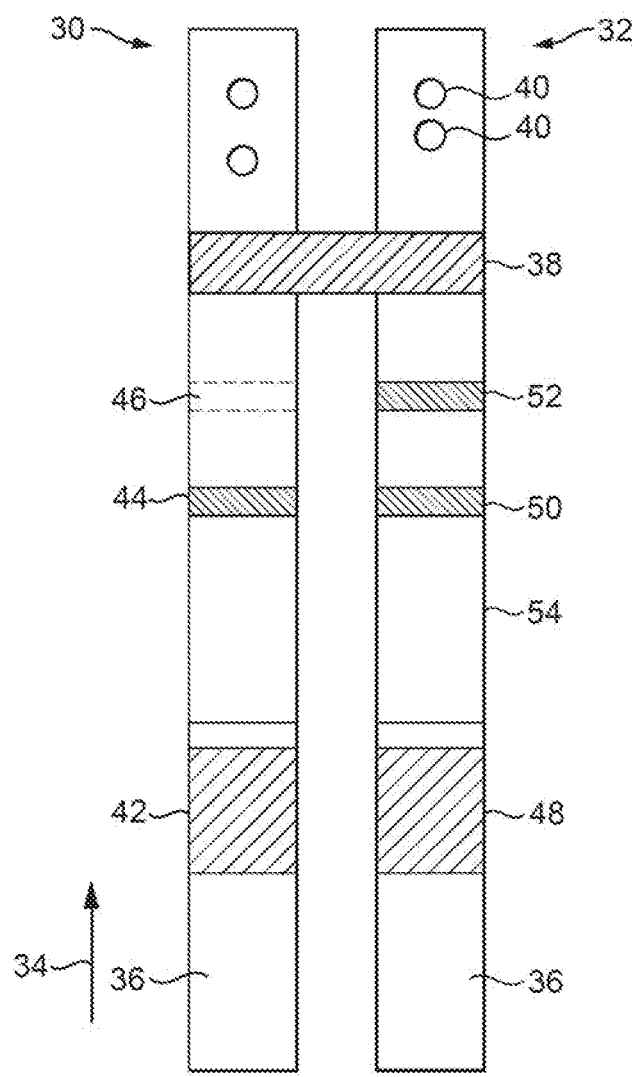
FIGS. 2-5 illustrate various formats of assay test strips for use in different embodiments of a device in accordance with the invention.

Referring to FIG. 2, this example relates to an embodiment in which two different lateral flow assay strips are used in combination with, or form an integral part of, a device in accordance with the invention.

In FIG. 2, one of the strips is used so perform a high sensitivity assay for hCG. The other strip, 32 is used to perform both an assay for FSH and for P3G. Urine sample enters both assay strips 30, 32 from a common sampling member (omitted for clarity) and flows along the strips in the direction indicated by the arrow 34. At their proximal ends (i.e. that end encountered first by a urine sample), both strips have a glass fibre conjugate pad 36 and, towards the distal end, both strips are in liquid flow communication with a highly absorbent "sink" 38 which encourages sample to flow along the assay strips. Both strips also comprise, beyond 'sink' 38, a pair of registration holes 40. These facilitate correct positioning of the strips within the device so that, in particular, the assay strips can be correctly read by the assay reading components of the device. Note that the pairs of registration holes 40 are not symmetrical, so the strips cannot be inadvertently swopped for each other.

Referring to strip 30, the conjugate pad 36 is loaded with a mobilisable anti-alpha hCG subunit monoclonal antibody, conjugated to a gold sol (42). This conjugate is dried on the conjugate pad and released upon wetting by the sample.

The detection zone 44 comprises an immobilized monoclonal antibody specific for the β subunit of hCG. Thus, any hCG present in the sample binds the labelled conjugate and forms a sandwich with the 'capture' anti-hCG β antibody at the detection zone, in a way which will be familiar to those skilled in the art.

The zone 46 bound by the dotted lines indicates a reference zone, which the assay result reading means uses to calibrate the assay readings. The same reference zone 46 may be used to calibrate both the hCG assay readings and also the readings obtained for the FSH and P3G assays on strip 32 (i.e. a common reference zone may be used).

Referring to strip 32, the glass fibre conjugate pad has two different conjugates 48: one is a gold sol conjugated to an anti-FSH α subunit monoclonal antibody and the other is a gold sol conjugated to an anti-P3G monoclonal antibody. (In this example, the anti-hCGα and anti-FSHα are the same antibody clone).

An immobilized anti-FSH β subunit monoclonal antibody is used as the capture antibody at FSH detection zone 50, whilst an immobilized P3G-Ovalbumin conjugate is used as the capture molecule at P3G detection zone 52.

The main body of each assay strip 30, 32 is formed of nitrocellulose, as indicated by reference numeral 34.

Although in this embodiment the P3G detection zone 52 is shown downstream of the FSH detection zone 50, it can be envisaged that the relative positions of the two detection zones may be reversed.

A further variant is a format in which the hCG and P3G assays are performed on one strip, and a separate strip is used for the FSH assay.

Example 4A

Another assay format can be envisaged. This is essentially identical to that depicted in FIG. 2 and described in example 4, except that in this variant, one of the mobilisable conjugates deposited on conjugate pad 36 is a gold sol labelled with P3G-ovalbumin conjugate (instead of anti-P3G mAb) and the immobilized capture molecule at P3G detection zone 52 is immobilized anti-P3G mAb. In this arrangement, P3G in the sample competes with the labelled conjugate for binding to the capture antibody at the detection zone 52.

Example 5

Figure 3:
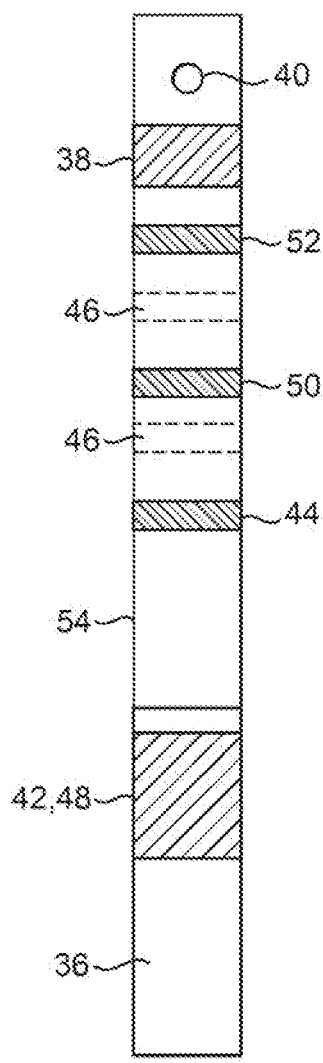

Referring to FIG. 3, (in which like components share the reference numerals used in FIG. 2) in this embodiment all 3 assays are performed using a single assay strip. The glass fibre conjugate pad 36 is loaded with a common anti-hCGα and anti-FSHα gold sol conjugate and an anti-P3G mAb gold sol conjugate (42, 48 respectively).

The hCG detection zone 44 comprises an immobilized anti-hCG β mAb. The FSH detection zone 50 comprises as immobilized anti-FSH β mAb, and the P3G detection zone 52 comprises an immobilized P3G-Ovalbumin conjugate.

As before, the relative positions of the detection zones may be altered. Also, as in Example 4A, the mobile P3G reagent may be a gold sol labelled with a P3G-Ovalbumin conjugate and the P3G detection zone 52 may comprise an immobilized anti-P3G antibody.

Yet another variant can be readily envisaged, in which the mobilisable conjugates may comprise a first gold sol conjugated to a β subunit-specific monoclonal antibody against hCG and a second gold sol conjugated to a β subunit specific monoclonal antibody against FSH. The respective detection zones comprise immobilized anti-hCGα and anti-FSHα antibodies. Another potential variant is to use an anti-hCG β subunit antibody in both the mobilisable conjugate and as the immobilised capture antibody, provided that the two antibodies bind to different epitopes and do not thus interfere or compete with each other for binding to hCG. FSB can also be assayed in a similar manner using anti-FSH β subunit specific antibodies on both the mobilisable conjugate and as the immobilized capture antibody.

Example 6

Figure 4:
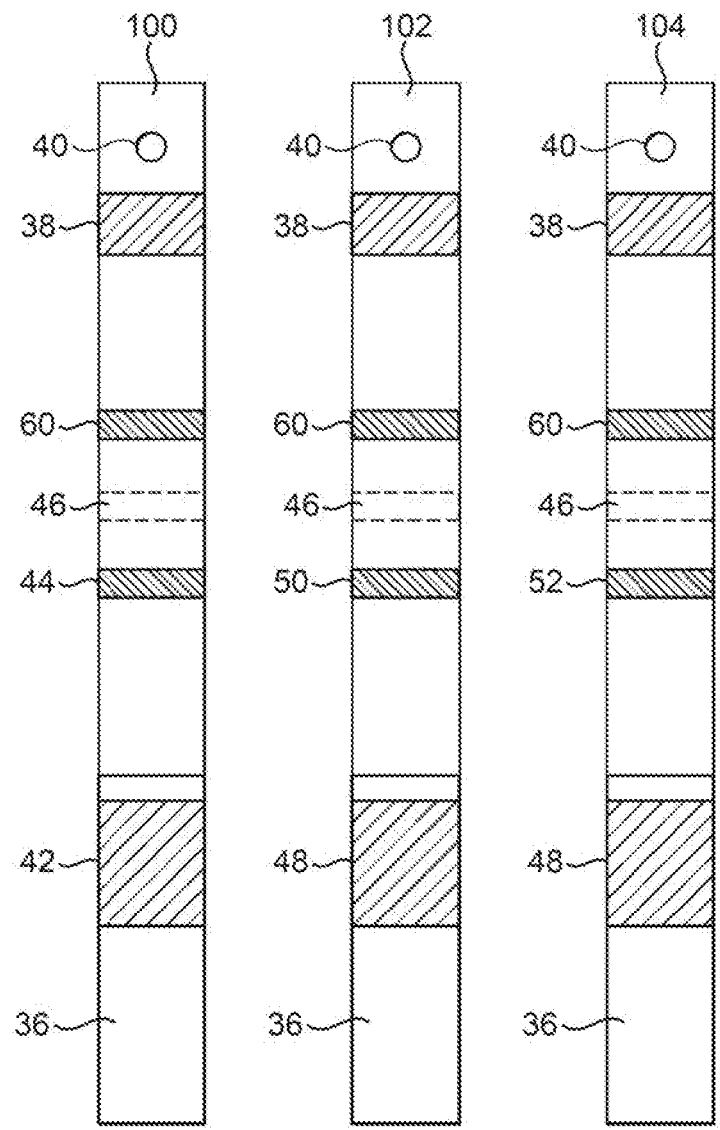

In this example, illustrated schematically in FIG. 4, a separate lateral flow assay strip is provided for each analyte. hCG is assayed on strip 100, FSH is assayed on strip 102, and P3G is assayed on strip 104. Like components share the same reference numerals as FIG. 2.

Sample is applied to all three assay strips via a common sampling member (omitted for clarity). A common 'sink' pad 38 is in liquid flow contact towards the distal end of each assay strip. In contrast to FIG. 2, in this embodiment each assay strip 100, 102, 104 has its own reference zone 46. In addition, each assay strip has a procedural control zone 60, which indicates if the assay has been performed correctly, to the extent that the binding reagents have retained their binding properties.

Example 7

Figure 5:
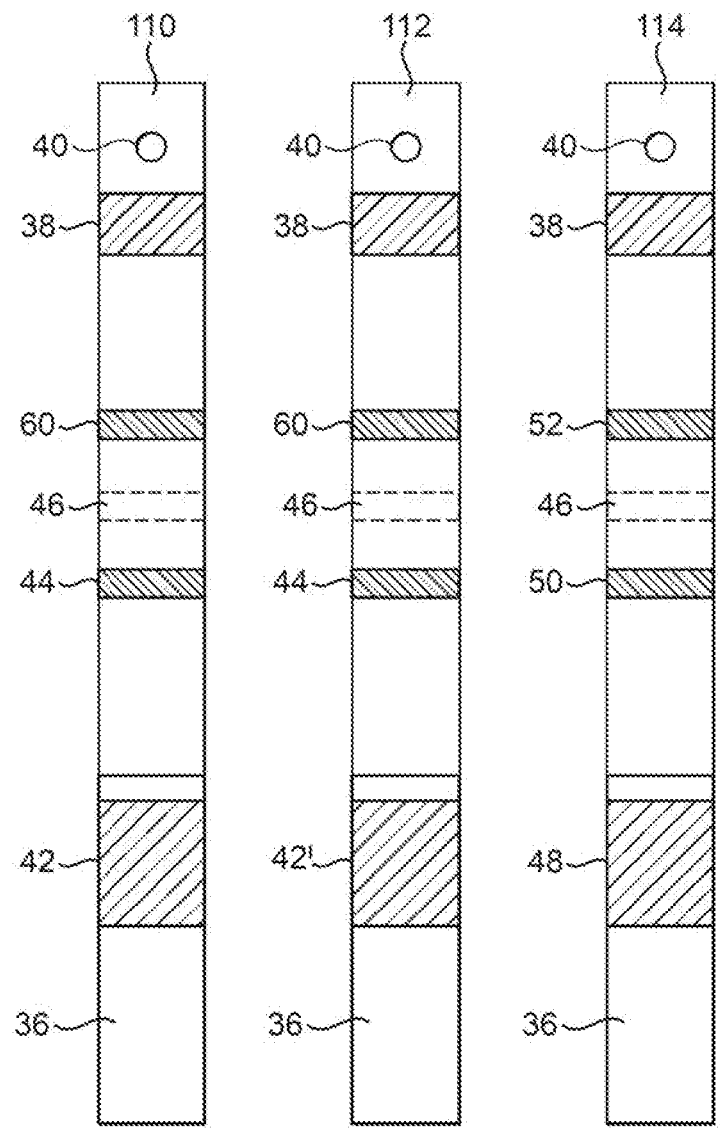

Yet another embodiment is illustrated in FIG. 5. This also utilises three assay strips. However two of the three strips are for measuring hCG levels, thus one of the strips 110 is a high sensitivity hCG assay (for detecting low levels of hCG) one of the strips 112 is a low sensitivity hCG assay (for detecting high levels of hCG), and the third strip 114 is for assaying both FSH and P3G. Like components are indicated by reference numerals common to FIG. 2.

In order to decrease the sensitivity of the hCG assay on strip 112, the conjugate pad 36 is loaded (42') not only with a mobilisable gold sol conjugated to an anti-hCGα mAb, but also a free (unlabeled) anti-hCG β mAb, which binds to hCG present in the sample and thus competes with the immobilized anti-hCG β capture antibody located at the detection zone 44. Thus, at high levels of hCG analyte in the sample, the assay system is not swamped. In this instance the unlabeled anti-hCG β monoclonal antibody is acting as a "scavenger" agent. The scavenger agent need not be an antibody but could be any unlabeled agent that binds to hCG and prevents it (indirectly) depositing labelled reagent at the detection zone. The scavenger agent may for example be immobilised on/in the flow path, or may be mixed (in mobilisable form) with the labelled conjugate.

The use of both high and low sensitivity hCG assays allows the device to measure hCG accurately over an extended concentration range, and this arrangement is useful in those embodiments in which the device is able to display a result showing not only that the subject is pregnant but also able to indicate to the user a quantitative estimate of how long the subject has been pregnant (e.g. in terms of weeks from conception).

Although the foregoing examples illustrate the use of various lateral flow assay formats, it will be apparent that an analogous assay arrangement could utilize a microfluidics-based assay, or an assay based on both lateral flow and microfluidics.

Example 8

This example describes the stops in the production of lateral flow assay strips suitable for use in a device in accordance with the invention as illustrated in FIG. 4.
Production of Assay Reagents:
A. Preparation of Gold Sol Labelled Antibody:
1. P3G Assay:
Method:
Borate buffer (20 ml, 20 mM, pH 8.5) was added to 80 nm gold sol solution (20 ml, $A_{550}$ nm=OD 6.85, BBI International) to give final solution containing gold sol at OD 3.425 in 10 mM borate buffer.

A solution of anti P3G antibody (Clone #5806:2, Alere San Diego, 40 ml, 160 µg/ml in 10 mM borate buffer) was mixed rapidly with the gold sol solution on a magnetic stirrer for 30 mins at room temperature.

After 30 min mixing, 610 µl of a 65.6 mg/ml β-casein solution was added to the reaction mixture and mixing was continued for a further 30 min at room temperature.

The final concentration of β-casein in the reaction mixture was 0.5 mg/ml.

The sol solution was poured into falcon tubes (50 ml) and the solutions centrifuged (4,000 g, 10 min, 15° C.).

The clear supernatants were decanted and the pelleted sol was vortexed and sonicated.

The sol solutions were transferred to eppendorf tubes and centrifuged (4,000 g, 7 min, 15° C.).

The supernatants were carefully removed and the pelleted sol was vortexed and sonicated, wash buffer was added (1 ml, 0.5 mg/ml β-casein in 10 mM borate buffer) to re-suspend the sol. After re-suspension the solutions were centrifuged (4,000 g, 7 min, 15° C.)

The supernatants were carefully removed and the pelleted sol was vortexed and sonicated, wash buffer was added (1 ml, 0.5 mg/ml β-casein in 10 mM borate buffer) to re-suspend the sol. After re-suspension the solutions were centrifuged (4,000 g, 7 min, 15° C.)

The supernatant was removed and the pelleted sol was vortexed and sonicated, the sol was re-suspended in a small volume of storage buffer (0.5 mg/ml BSA in PBS+azide [PBSA]) and the final volume adjusted to 2 mls. Although initial experiments used 0.5 mg/ml BSA in the storage buffer, it was found that the presence of BSA interfered with the P3G assay. Subsequently therefore 0.5 mg/ml casein was used in the storage buffer in place of BSA. In embodiments of the invention where the P3G assay components might come into contact with components of other assays (e.g. where both a P3G assay and an hCG and/or FSH assay are performed on a single assay flow path or lateral flow strip), then it will be necessary for the other assays also to avoid the use of BSA, to prevent the P3G assay being affected.

The final OD of the sol preparation was determined by measuring the absorbance at 550 nm.

2. hCG Assay & FSH Assay:
Method:

Borate buffer (20 ml, 20 mM, pH8.5) was added to 80 nm gold sol solution (20 ml, $A_{550}$ nm=OD 6.85, BBI International) to give final solution containing gold sol at OD 3.425 in 10 mM borate buffer.

A solution of anti α-hCG antibody (Clone #3299:4, Alere San Diego, 40 ml, 20 µg/ml in 10 mM borate buffer) was mixed rapidly with the gold sol solution on a magnetic stirrer for 30 mins at room temperature.

After 30 min mixing, 610 µl of a 65.6 mg/ml β-casein solution was added to the reaction mixture and mixing was continued for a further 30 min at room temperature. The final concentration of β-casein in the reaction mixture was 0.5 mg/ml.

The sol solution was poured into falcon tubes (50 ml) and the solutions centrifuged (4,000 g, 10 min, 15° C.).

The supernatants were decanted and the pelleted sol was vortexed and sonicated.

The sol solutions were transferred to eppendorf tubes and centrifuged (4,000 g, 7 min, 15° C.).

The supernatants were carefully removed and the pelleted sol was vortexed and sonicated, wash buffer was added (1 ml, 0.5 mg/ml β-casein in 10 mM borate buffer) to re-suspend the sol. After re-suspension the solutions were centrifuged (4,000 g, 7 min, 15° C.).

The supernatants were carefully removed and the pelleted sol was vortexed and sonicated, wash buffer was added (1 ml 0.5 mg/ml β-casein in 10 mM borate buffer) to re-suspend the sol. After re-suspension the solutions were centrifuged (4,000 g, 7 min, 15° C.).

The supernatant was removed and the pelleted sol was vortexed and sonicated, the sol was re-suspended in a small volume of storage buffer (0.5 mg/ml BSA in PBSA) and the final volume adjusted to 2 mls.

The final OD of the sol preparation was determined by measuring the absorbance at 550 nm.

B. Preparation of Reagents to be Immobilised onto Nitrocellulose:

Although the example below describes the preparation and us of P3G conjugates of ovalbumin, it can be envisaged that other proteinaceous or synthetic polymeric conjugates of P3G may be employed. Protein conjugates of P3G include but are not limited to bovine serum albumin, immunoglobulin G, gelatin and beta-casein. Representative examples of polymeric carriers include polyallyl amine, polyvinyl alcohol, poly lysine, and polyethylene imine.

P3G Assay:

Preparation of P3G conjugates of ovalbumin (10:1 molar ratio of P3G to Ovalbumin)

Method

Preparation of NHS activated P3G ester (10 mg P3G, 10% DMSO Scale)

The water soluble carbodiimide, EDC was used for the preparation of the NHS activated P3G ester. The reaction was carried out with a molar excess of EDC (1.1×) and NHS (1.5×) over P3G ($2.0136 \times 10^{-5}$ moles P3G).

The total volume for carrying out the reaction was 600 µl.

A 14.153 mg/ml solution of EDC (1-Ethyl-3-[3-dimethylaminopropyl]carbodimide hydrochloride, Thermo Scientific, Cat #77149, M.W.=191.7) was prepared by dissolving 48 mg of EDC in 3.39 ml of DMSO (99.7% Extra dry, Acros, Cat #3484400).

An 11.6 mg/ml solution of NHS (N-Hydroxysuccinimide, Sigma Aldrich, Cat #130072, M.W.=115.09) was prepared by dissolving 29 mg of NHS in 2.5 ml of DMSO.

10 mgs of P3G (5β-Pregnane-3α, 20α-diol glucuronide, P3G, Sigma, Cat # P3635, M.W.=496.63) was weighed out in a glass vial and 300 µl of the EDC and 300 µl of the NHS solutions prepared above wen added to give a reaction mixture containing 1.1× more EDC and 1.5× more NHS than P3G. The reaction mixture was stirred at room temperature in the dark for 4 hours and reaction was allowed to proceed overnight (approx 16 hrs) at 20° C.

Dry DMSO (400 µl) was added to the above solution to make up the total volume of solution to 1000 µl.

Assuming 100% conversion of P3G to P3G-NHS ester, there will be $2.0136 \times 10^{-5}$ moles of activated ester in 1000 µl. Thus, 100 µl of this solution will contain $2.0136 \times 10^{-6}$ moles.

Preparation of P3G-Ovalbumin Conjugate

100 µl of the active aster ($2.0136 \times 10^{-6}$ moles) was used.

A 4.43 mg/ml solution of Ovalbumin (Sigma, Cat # A5503>98%, MW=44,000) in PBS buffer (PBS tablets, Sigma, Cat # P4417) was prepared by dissolving 92.4 mg Ovalbumin in 20.858 ml PBS and 2 ml of this solution was used for the 10-fold preparation.

DMSO (100 µl) was added to the Ovalbumin solution, just prior to the addition of the NHS activated P3G solution (100 µl). Thus, the final concentration of DMSO in the reaction mixture was maintained at 10% (v/v).

The reaction solution was stirred at room temperature for 3.5 hours. After 3.5 hours reaction, the reaction was quenched by addition of 1 M Iris buffer pH 7.4 (100 µl) to the solution.

The P3G-Ovalbumin was then centrifuged and the clear supernatant was removed and purified on a PD-10 column (GE Healthcare, Cat #17-0851-01) pre-equilibrated with PBSA.

The conjugate solution (2.5 ml) was applied to the top of the equilibrated column and all the solution was allowed to drain into the gel bed.

Elution buffer (PBSA, 3 ml) was then applied to the column and the flow through was collected into a clean glass vessel. This flow through contained the purified P3G-Ovalbumin conjugate.

An Extinction coefficient ($A_{280}^{0.1\%}$) of 0.7 was used for determining the protein concentration. The P3G-Ovalbumin conjugate was then concentrated to 3 mg/ml for immobilisation on Nitrocellulose.

1. hCG Assay:

Anti β-hCG antibody (Clone #3468:2, Alere San Diego) was diluted in PBSA to 3 mg/ml prior to immobilisation onto Nitrocellulose.

2. FSH Assay:

Anti β-FSH antibody (Clone #5948:2, Alere San Diego) was diluted in PBSA to 3 mg/ml prior to immobilisation onto Nitrocellulose.

C. Preparation and Means for Locating & Immobilising Specific Binding Substances:

Method

1. P3G Assay:
1.1 A PVA blocking buffer (pH 9) was prepared (Tris Base 20 mM (Sigma), PVA 1% w/v (PVA 80% hydrolysed, 9-10K MW (Sigma, Tween 20 0.05% w/v (Sigma) & NaCl 150 mM (Sigma)).
1.2 A PVA blocking solution was prepared by addition of 2% w/v of Sucrose (Sigma) to 47.5 mls of the PVA blocking buffer with addition of 2.5 mls of Ethanol (Sigma).
1.3 While backed Nitrocellulose (Whatman) sheets were cut to 35 cm*40 mm bands using a press cutter and hole pouched at one end of the band to a pitch of from (many different dimension of pitch could be used, however for the examples presented here a 6 mm hole pitch was used).
1.4 A biodot plotter was set up to plot the P3G-Ovalbumin Conjugate at the desired location on the Nitrocellulose band at a concentration of 3 mg/ml with a plot rate of 1 μl/cm.
1.5 After plotting, the bands were dried at 55° C. and blocked using the PVA blocking solution and then dried at 65° C. and stored overnight at room temperature with desiccant in sealed foil pouches.

2. hCG Assay:
Steps 1.1 to 1.3 inclusive were followed from section.C.1.
A biodot plotter was set up to plot the 3468. Antibody at the desired location on the Nitrocellulose band at a concentration of 3 mg/ml with a plot rate of 1 μl/cm.
After plotting the bands were dried at 55° C., and blocked using the PVA blocking solution and then dried at 65° C. and stored overnight at room temperature with desiccant in sealed foil pouches.

3. FSH Assay:
Steps 1.1 to 1.3 inclusive were followed from section.C.1.
A biodot plotter was set up to plot the 5948 Antibody at the desired location on the Nitrocellulose band at a concentration of 3 mg/ml with a plot rate of 1 μl/cm.
After plotting the bands were dried at 55° C. and blocked using the PVA blocking solution and to dried at 65° C. and stored overnight at room temperature with desiccant in sealed foil pouches.

D. Preparation and Means for Immobilising Gold-Sol Labelled Binding Reagents (for Use in Example of Embodiment 1):

Method

1. P3G Assay:
The 5806 coated Sol Conjugate, prepared in section.A.1 was spun down in a centrifuge and the supernatant was removed. The resulting pellet was vortexed and sonicated and then the pellet was reconstituted in a gold-sol conjugate spray buffer to the desired OD of Gold (in this example OD80). The gold sol conjugate spray buffer (pH 7.6) used in the following examples contained 10 mM Tris (Sigma), 5% w/v Sucros (Sigma) & 0.5% (w/v) BSA*(Proliant Biologicals, SKU #68700). However, other examples of spray buffers that also can be used, may have additional substances in the diluent solution and may also have higher or lower levels of constituents listed in the above example. (Subsequently altered to 0.5% w/v casein).

G041 Millipore Glass Fibre (Surewick®) was cut to 26 mm*35 cm and loaded onto a Biodot Spray Rig.

The biodot spray rig was set up to impregnate/infuse the glass fibre with 5806 coated Sol Conjugate at the desired location on the glass fibre. In this example, the glass fibre was sprayed with 4 sequential passes of the OD80 Conjugate with a plot rate of 1.65 μl/cm on each spray pass.

The gold sol infused glass fibre was dried at 55° C. and stored overnight at room temperature with desiccant in sealed foil pouches.

2. hCG Assay:
Gold sol impregnated/infused glass fibre bands for the hCG assay were prepared in an identical manner to the above except that 3299 coated gold sol (see section A.2) was used here and the OD of the sol conjugate was OD111. In the example cited here the glass fibre was sprayed with 2 passes of gold conjugate at a plot rate of 1.65 μl/cm.

3. FSH Assay:
For the FSH assay, 3299 coated gold sol (see Section A.2) was sprayed on glass fibre using 2 sequential passes of OD62 gold conjugate at a dose rate of 1.65 μl/cm. Dosed bands were dried and stored in an identical manner to the above example.

E. Assay Strip Construction/Production: Examples of Single Strip Assay Chip Constructs (One Assay Per Chip/Strip)

Method

1. P3G Assay:
The P3G assay components were assembled into an assay chip (strip) with the aid of a kinematic Universal Laminator Module assembly unit.

Backing laminate (Ferrisgate) was placed onto the kinematic card platen and a blocked Nitrocellulose band with immobilised P3G-Ovalbumin (section C.1) was affixed to the backing laminate at a predetermined position.

A band of 5806 Sol conjugate infused glass fibre (section D.1) was affixed to the backing laminate with a 2 mm overlap over the nitrocellulose band.

A roller mat ensured good contact of all the components of the chip with the backing laminate.

The bands were then cut into 6 mm individual chips using a Biodot cutter and stored with desiccant in foil pouches until ready for use.

2. hCG Assay:
The hCG assay components were assembled in an identical manner to the P3G assay except for the use of nitrocellulose bands immobilised with 3468 (section C.2) and glass fibre bands impregnated with 3299 gold sol conjugate (section D.2).

The bands were then cut into 6 mm individual chips using a Biodot cutter and stored with desiccant in foil pouches until ready for use.

3. FSH Assay:
The FSH assay components were assembled in an identical manner to the P3G assay except for the use of nitrocellulose bands immobilised with 5948 (section C.3) and glass fibre bands impregnated with 3299 gold sol conjugate (section D.3).

The bands were then cut into 6 mm individual chips using a Biodot cutter and stored with desiccant in foil pouches until ready for use.

Example 9

In this example, further information is provided on illustrative algorithms of use in a device in accordance with the invention.

The assay device of the invention provides a higher pregnancy detection rate before the day of the expected period compared to conventional self-use pregnancy tests, whilst retaining specificity for pregnancy. It achieves this by not only having a greater sensitivity for hCG, but also by measuring FSH and one or more progesterone metabolites, in order to retain specificity for pregnancy at very low hCG concentrations; elevated levels of hCG can be seen in some post- and peri-menopausal women which could generate false positive results with an overly sensitive hCG test. FSH acts as a rule-out for pregnancy, as high levels are associated with peri- and post-menopausal status, whilst progesterone metabolites (e.g. P3G) act as a rule—in for pregnancy as elevated levels are seen in pregnancy.

In one simple embodiment of this concept, the device might function as outlined in Table 2 below. In this example the progesterone metabolite assayed is P3G:

TABLE 2

| hCG Assay | FSH Assay | P3G Assay | Result |
|---|---|---|---|
| hCG ≥ Upper hCG threshold | N/A | N/A | PREGNANT |
| hCG ≥ Lower hCG threshold and < Upper hCG threshold | FSH < FSH threshold | P3G ≥ P3G threshold | PREGNANT |
| | | P3G < P3G threshold | NOT PREGNANT* |
| | FSH ≥ FSH threshold | P3G ≥ P3G threshold | NOT PREGNANT* |
| | | P3G < P3G threshold | NOT PREGNANT |
| hCG < Lower hCG threshold | N/A | N/A | NOT PREGNANT |

*It is envisaged that the probability of instances in which conflicting FSH and progesterone metabolite assay results arise will be very low. The device will typically be programmed to declare a "NOT PREGNANT" result in such circumstances, and/or the user may be instructed to test again at a later stage.

All tests are specified as tests of assay and are expressed in terms of detected concentration. For tests of the intensity of a developed visible line, the logic must be inverted for competition assays where the intensity of the line reduces with increasing analyte concentration.

Improved performance could possibly be achieved by using a more extensive algorithm: the importance (weighting) of the level of FSH or progesterone metabolite levels could depend on the level of hCG and/or the thresholds used for testing FSH and progesterone metabolite used could depend on the level of hCG. In a more complex case the FSH threshold could depend on the hCG concentration and the progesterone metabolite threshold could depend on the FSH level (and vice-versa).

The algorithm is represented schematically in FIG. 6. Referring to that Figure, the algorithm/logic tree concerns an embodiment of the test device of the invention comprising two lateral flow test strips. A first strip is used to perform an assay for hCG and a second strip is used to perform an assay for FSH and an assay for P3G.

In the logic tree, the assay result reader first examines the hCG assay result, and compares the assay signal with a predetermined signal value corresponding to an hCG concentration of 2.5 mIU/ml. If the assay result is less than the 2.5 mIU/ml threshold, the reader may immediately indicate that the test subject is "Not Pregnant" (following the symbol in the Figure). [The outcome of the overall assay (i.e. "Pregnant" or "Not Pregnant") may not necessarily be indicated to a user, however, until the results of all three analyte assays have been determined]. Alternatively, if the determined hCG concentration in the urine sample is equal to or greater than the 2.5 mIU/ml threshold, the reader proceeds to check the FSH assay result (the first test line or detection zone on the second assay strip). Since an hCG concentrate above 2.5 mIU/ml might be due to non-pregnancy related sources, an "early" determination of the overall outcome of the assay might not be possible based solely on the hCG assay result.

The FSH assay has a threshold of 10 mIU/ml. If the determined FSH concentration in the sample is equal to or greater than the 10 mIU/ml threshold, the assay device/reader declares the result of the test as "Not Pregnant". Conversely, if the FSH concentration in the sample is above the 10 mIU/ml threshold, the assay device/reader will continue to examine the P3G assay result.

The P3G assay result is read from the second test line or detection zone on the second lateral how assay strip. If the P3G assay indicates that the P3G concentration in the sample is less than 4 μg/ml, then the subject is declared to be "Pregnant".

It will be apparent to those skilled in the art that the precise signal values or threshold concentrations selected for a particular embodiment will depend, at least in part, on the specific characteristics of the assays employed (e.g. reagents, flow matrices, concentration of conjugates etc.), such that the thresholds identified above might be slightly different in other embodiments, although the relative amounts will generally be the same.

Further, the Figure shows the assay device/reading means inspecting or checking the results of the hCG, FSH and P3G assays sequentially. It will be apparent that the respective assay results may be inspected in any order, or substantially simultaneously. Further, an "early" determination of one or two assay results may enable a determination of the outcome of the overall assay result (i.e. "Pregnant" or "Not Pregnant") without necessarily requiring the result of all three analyte assays to be known, if the concentrations of the analytes are very much above (or below, as appropriate) the relevant threshold concentrations.

What is claimed is:

1. A test device to detect pregnancy in a human female, the test device comprising:
    a first pregnancy marker detection zone configured to receive a urine sample and to produce a signal corresponding to the amount of the first pregnancy marker in the urine sample obtained from the female;
    a second pregnancy marker detection zone configured to receive the urine sample and to produce a signal corresponding to the amount of the second pregnancy marker in the urine sample;
    a third pregnancy marker detection zone configured to receive the urine sample and to produce a signal corresponding to the amount of the third pregnancy marker in the urine sample; and
    a detection system, comprising a microprocessor, the detection system configured to receive the signals produced by the first, second, and third pregnancy marker detection zones and to determine the amount of the first, second, and third pregnancy markers in the urine sample based on the respective signals produced by the first, second, and third pregnancy marker detection zones;
wherein the microprocessor is configured (a) if the amount of the first marker exceeds a first predetermined threshold, to determine the presence of pregnancy in the human female without use of or reference to a previous measurement or to the presence or amount of at least one of the second pregnancy marker and the third pregnancy marker and (b) if the amount of the first marker falls below a second predetermined threshold, which is lower than the first predetermined threshold, to determine the absence of pregnancy in the female without use of or reference to a previous measurement or to the presence or amount of at least one of the second pregnancy marker and the third pregnancy marker.

2. The test device of claim 1, wherein the microprocessor is configured, if the amount of the first pregnancy marker is (i) equal to or greater than the second predetermined threshold and (ii) equal to or less than the first predetermined threshold to determine the presence of pregnancy only if (x) the amount of the second pregnancy marker falls below a third predetermined threshold and (y) the amount of the third pregnancy marker exceeds a fourth predetermined threshold.

3. The test device of claim 2, wherein the microprocessor is configured to determine the absence of pregnancy in the human female if either or both (x) the amount of the second pregnancy marker exceeds the third predetermined threshold or (y) the amount of the third pregnancy marker falls below the fourth predetermined threshold.

4. The test device of any one of claims 1-3, wherein the microprocessor is configured to determine the amount of the second and third pregnancy markers only if the amount of the first pregnancy marker is (i) equal to or greater than the second predetermined threshold and (ii) equal to or less than the first predetermined threshold.

5. The test device of claim 4, wherein the first pregnancy marker is a marker indicative of the presence of an embryo in a human female, the second pregnancy marker is a marker indicative of folliculargenesis or other follicular growth or activity in a human female, and the third pregnancy marker is a marker indicative the maintenance of a pregnancy of the female.

6. The test device of claim 5, wherein the first pregnancy marker is hCG or a metabolite thereof, the second pregnancy marker is follicle stimulating hormone (FSH), leutinizing hormone (LH), or inhibin B, or a metabolite thereof, and the third pregnancy marker is pregnanediol-3-glucuronide (P3G) or a metabolite thereof.

7. The test device of claim 4, wherein the first pregnancy marker hCG or a metabolite thereof, the second pregnancy marker is follicle stimulating hormone (FSH), leutinizing hormone (LH), or inhibin B, or a metabolite thereof, and the third pregnancy marker is pregnanediol-3-glucuronide (P3G) or a metabolite thereof.

8. The test device of any one of claims 1-3, wherein the first pregnancy marker is a marker indicative of the presence of an embryo in a human female, the second pregnancy marker is a marker indicative of folliculargenesis or other follicular growth or activity in a human female, and the third pregnancy marker is a marker indicative of the maintenance of a pregnancy of the female.

9. The test device of claim 8, wherein the first pregnancy marker hCG or a metabolite thereof, the second pregnancy marker is follicle stimulating hormone (FSH), leutinizing hormone (LH), or inhibin B, or a metabolite thereof, and the third pregnancy marker is pregnanediol-3-glucuronide (P3G) or a metabolite thereof.

10. The test device of any one of claims 1-3, wherein the first pregnancy marker is hCG or a metabolite thereof, the second pregnancy marker is follicle stimulating hormone (FSH), leutinizing hormone (LH), or inhibin B, or a metabolite thereof, and the third pregnancy marker is pregnanediol-3-glucuronide (P3G) or a metabolite thereof.

\* \* \* \* \*